US010460827B2

(12) United States Patent
Neshich et al.

(10) Patent No.: US 10,460,827 B2
(45) Date of Patent: Oct. 29, 2019

(54) IDENTIFICATION OF THERAPEUTIC TARGETS FOR COMPUTER-BASED DESIGN OF DRUGS AGAINST BACTERIA CONTAINING THE PILT PROTEIN

(75) Inventors: Goran Neshich, Campinas (BR); Izabella Agostinho Pena Neshich, Campinas (BR); Jose Gilberto Jardine, Campinas (BR); Leticia Nishimura, Campinas (BR); Ivan Mazoni, Campinas (BR); José Salim, Campinas (BR)

(73) Assignee: EMPRESA BRASILEIRA DE PESQUISA AGROPECUARIA, Plano Piloto, Brasilia DF (BR)

( * ) Notice: Subject to any disclaimer, the term of this patent is extended or adjusted under 35 U.S.C. 154(b) by 568 days.

(21) Appl. No.: 13/821,792

(22) PCT Filed: Sep. 8, 2011

(86) PCT No.: PCT/BR2011/000317
§ 371 (c)(1),
(2), (4) Date: Jul. 1, 2013

(87) PCT Pub. No.: WO2012/031343
PCT Pub. Date: Mar. 15, 2012

(65) Prior Publication Data

US 2013/0324425 A1 Dec. 5, 2013

(30) Foreign Application Priority Data

Sep. 8, 2010 (BR) .................................... 1003646

(51) Int. Cl.
*G16B 15/00* (2019.01)
*G16B 20/00* (2019.01)

(52) U.S. Cl.
CPC ............ *G16B 15/00* (2019.02); *G16B 20/00* (2019.02); *Y02A 90/26* (2018.01)

(58) Field of Classification Search
None
See application file for complete search history.

(56) References Cited

U.S. PATENT DOCUMENTS

| | | | | |
|---|---|---|---|---|
| 2003/0158672 | A1* | 8/2003 | Ramnarayan et al. ......... | 702/19 |
| 2004/0034481 | A1* | 2/2004 | Hurst .............................. | 702/27 |
| 2007/0055459 | A1* | 3/2007 | Coen et al. ..................... | 702/19 |

OTHER PUBLICATIONS

Satyshur et al. et al. Structure, 2007,15, vol. 363-376.*
Mattick et al. Annu. Rev. Microbiol., 56, 289-304, 2002.*
Sali et al. J. Mol. Biol., 1993,234, 779-815.*

* cited by examiner

*Primary Examiner* — Michael L Borin
(74) *Attorney, Agent, or Firm* — Sughrue Mion, PLLC

(57) ABSTRACT

The present invention relates to a method for identifying target regions existing in the interface of monomers constituting the PilT protein with the view to design molecules potentially applicable in impairing the activity of this protein, thus controlling infectious processes. The method is characterized in (i) selecting at least one amino acid sequence constituting the PilT monomer; (ii) developing a three-dimensional computational model of the PilT homohexameric structure; (iii) analyzing and determining, with computer aid, the interface-forming residues (IFR) and their physicochemical and structural characteristics for all the chains of the models of hexameric complexes generated; (iv) selecting the regions to be used as therapeutic targets (and preferred therapeutic targets) in the interface between the monomers based on the intensity of determined parameters; (v) computer-aided design of molecules potentially capable of effecting bindings and/or interactions between target regions of the monomers. Markedly, some of the main applications of this technology consist in combating the bacteria *Xylella fastidiosa*, an etiologic agent of the Citrus Variegated Chlorosis (CVC or "Amarelinho"), and Pierce's disease.

1 Claim, 10 Drawing Sheets

Specification includes a Sequence Listing.

E89C4m4

E89C4m29

E89C4m30

E89C4m32

E89C4m34

IDENTIFICATION OF THERAPEUTIC TARGETS FOR COMPUTER-BASED DESIGN OF DRUGS AGAINST BACTERIA CONTAINING THE PILT PROTEIN

FIELD OF THE INVENTION

The present application relates to a method for identifying target regions existing in the interface of monomers constituting the PilT protein with a view to design molecules that are potentially applicable in impairing the activity of this protein, thus controlling infectious processes. Markedly, one of the main applications of this technology consists in combating the bacteria *Xylella fastidiosa*, an etiological agent of Citrus Variegated Chlorosis (CVC or "Amarelinho") and Pierce's disease.

PRIOR ART

A *Xylella fastidiosa* is a gram-negative and non-flagellated bacterium that causes various diseases on plants, such as Citrus Variegated Chlorosis (CVC), popularly known as "amarelinho" and the Pierce's disease, which affects the citriculture viniculture, respectively. The *Xylella fastidiosa* microorganism is limited to persist colonizing the xylem vessel, the vesses that conduct water and salts in plants, and in the anterior digestive tract of some insects, as those popularly known as "cigarrinhas" (hoppers) (Hemiptera: Cicadellidae), which feeds on plant sap and serve as vectors for carrying and inserting bacteria into plants (Hopkins, D. L., e A. H. Purcell. 2002. *Xylella fastidiosa*: cause of Pierce's disease of grapevine and other emergent diseases. Plant Dis. 86:1056-1066). Ever since years ago one has been testing the use of insecticide against the vector-insects of this bacterium, but there has been on sufficient efficacy, and the summed damages for the year 2000, resulting from the Pierce's disease, in the state of California, USA, have reached 14 billion dollars (see document US 2005/0257285). The virulence mechanisms of *Xylella fastidiosa* and the manner in which it interacts with the host plants are not totally known. However, the most plausible explanation is the formation of aggregates like biofilms which, upon colonizing the xylem, cause a blockage of the sap flow and culminates in the symptoms of the disease (Hopkins, D. L. 1989. Xylem limited bacterial pathogen of plants. Annu. Rev. Phytopathol. 27:271-290; Newman, K. L., R. P. P. Almeida, A. H. Purcell, and S. E. Lindow. 2003. Use of a green fluorescent strain for analysis of *Xylella fastidiosa* colonization of *Vitis vinifera*. Appl. Environ. Microbiol. 69:7319-7327).

Hopkins and co-workers suggested that the colonization and pathogenicity of the *Xylella fastidiosa* bacterium, which lead to the Pierce's disease, are strictly related to its capability of moving within the elements of the xylem vessel, which enables the colonization of other regions of the plant. Besides, it is known that the virulent and attenuated strains rarely move from the inoculation point (Hopkins, D. L. 1989. Xylem-limited bacterial pathogen of plants. Annu. Rev. Phytopathol. 27:271-290).

The genoma Project of *Xylella fastidiosa* disclosed the presence of genes that encode proteins involved in giogenesis and the function of type IV pili (T4P) (Yespson, A. J. G., F. C. Reinach, P. Arruda, F. A. Abreu, M. Acencio, R. Alvarenga, L. M. C. Alves, J. E. Araya, G. S. Baia, C. S. Baptista, M. H. Barros, E. D. Bonaccorsi, S. Bordin, J. M. Bove, M. R. S. Briones, M. R. P. Bueno, A. A. Camargo, L. E. A. Camargo, D. M. Carraro, H. Carrer, N. B. Colauto, C. Colombo, F. F. Costa, M. C. R. Costa, C. M. Costa-Neto, L. L. Coutinho, M. Cristofani, E. Dias-Neto, C. Docena, H. El-Dorry, A. P. Facincani, A. J. S. Ferreira, V. C. A. Ferreira, J. A. Ferro, J. S. Fraga, S. C. Franca, M. C. Franco, M. Frohme, L. R. Furlan, M. Garnier, G. H. Goldman, M. H. S. Goldman, S. L. Gomes, A. Gruber, P. L. Ho, J. D. Hoheisel, M. L. Junqueira, E. L. Kemper, J. P. Kitajima, J. E. Krieger, E. E. Kuramae, F. Laigret, M. R. Lambais, L. C. C. Leite, E. G. M. Lemos, M. V. F. Lemos, S. A. Lopes, C. R. Lopes, J. A. Machado, M. A. Machado, A. Madeira, H. M. F. Madeira, C. L. Marino, M. V. Marques, E. A. L. Martins, E. M. F. Martins, A. Y. Matsukuma, C. F. M. Menck, E. C. Miracca, C. Y. Miyaki, C. B. Monteiro-Vitorello, D. H. Moon, M. A. Nagai, A. Nascimento, L. E. S. Netto, A. Nhani, F. G. Nobrega, L. R. Nunes, M. A. Oliveira, M. C. de Oliveira, R. C. de Oliveira, D. A. Palmieri, A. Paris, B. R. Peixoto, G. A. G. Pereira, H. A. Pereira, J. B. Pesquero, R. B. Quaggio, P. G. Roberto, V. Rodrigues, A. J. D. Rosa, V. E. de Rosa, R. G. de Sa, R. V. Santelli, H. E. Sawasaki, A. C. R. da Silva, A. M. da Silva, F. R. da Silva, W. A. Silva, J. F. da Silveira, 2000. The genoma sequence of the plant pathogen *Xylella fastidiosa*. Nature 406:151-157), que podem gerar mobilidade do tipo "Twitching motility" (Meng, Y., Li, Y., Galvani, C. D., Hao, G., Turner, J. N., Burr, T. J. & Hoch, H. C. 2005. Upstream migration of *Xylella fastidiosa* via pilus-driven twitching motility. J Bacteriol 187, 5560-5567). "Twitching motility" is a form of movement associated to the surface, by which the bacteria pull themselves rapidly along the surfaces through polymerization and depolymerization cycles of the Pilus (T4P) (Skerker, J. M. & Berg, H. C. 2001. Direct observation of extension and retraction of type IV pili. Proc Natl Acad Sci USA 98, 6901-6904). The energi necessary for the movement is supplied by means of hydrolysis of ATP by proteins called PilB and PilT for mounting and dismounting the Pilus, respectively. The loss of function of the Pilus protein or of PilB results in the absence of this type of motility, coupled to deprival of extension or retraction of the pilus (Whitchurch, C. B., Hobbs, M., Livingston, S. P., Krishnapillai, V. & Mattick, J. S. 1991. Characterisation of a *Pseudomonas aeruginosa* twitching motility gene and evidence for a specialized protein export system widespread in eubacteria. Gene 101, 33-44).

Satyshur et al. 2007 (K. A. Satyshur, G. A. Worzalla, L. S. Meyer, E. K. Heiniger, K. G. Aukema, A. M. Misic, and K. T. Fore. Crystal Structures of the Pilus Retraction Motor PilT Suggest Large Domain Movements and Subunit Cooperation Drive Motility. Structure 15, 363-376. March 2007) carried out the structural characterization of the retraction motor of the pilus, PilT. These authors have resolved, by X-ray, four three-dimensional structures of PilT proteins (codes PDB: 2GSZ, 2EWV, 2EWW and 2EYU) of a hypertermophyle, *Aquifex aeolicus*. PilT is na hexameric ATPase of a subgroup of the "bacterial type II/type IV secretion systems", and has two large structural domains: the domain N-terminal (NTD) and the domain C-Terminal (CTD), which contains the ATPásico nucleus. Additionally, one demonstrated the remarkable importance of polar and carried interactions in the interfaces CTDn: NTDn+1 (1157 $Å^2$, of the 1782 $Å^2$ of the total interface area is supplied by the polar and carried residues) for the function of the PilT. Through the site-directed mutagenesis in *Pseudomonas aeruginosa*, they demonstrated that some residues are crucial to the function of the protein, half of them being located in the interface region (D29, R95 e R207) and pointed out the importance thereof to the proper functioning of the protein. The paper further mentions that this clarification is of the utmost importance to the development of tools that can prevent the spread of infectious diseases in animals and plants, caused by pathogens: *Ralstonia solanacearum*, cause agent of the moko or bacterial wilt on solanaceae plants (Kang, Y., Liu, H., Genin, S., Schell, M. A., and Denny, T. P. 2002). *Ralstonia solanacearum* requires type 4 pili to adhere to multiple surfaces and for natural transformation and virulence. Mol. Microbiol. 46, 427-437.), *Pseudomonas syringae* (there are more than 50 pathovars that act as pathogenic agents on various plants) (Hirano, S. S. e C.D. Upper. Bacteria in the Leaf Ecosystem with Emphasis on *Pseudomonas syringae*—a Pathogen, Ice Nucleus, and Epiphyte. Microbiology and Molecular Biology Reviews 64 624-653. 2000), *Pseudomonas aeruginosa* (an opportunist pathogen on human beings an also causes infections on plants such as basil (*Ocimum basilicum*) and lettuce (*Lactuca sativa*) (Rahme, L. G., Stevens, E. J., Wolfort, S. F., Shao, J., Tompkins, R. G., Calderwood, S. B., Ausube, I F. M. 1995. Common virulence factors for bacterial pathogenicity in plants and animals. Science 268: 1899-1902), *Neisseria meningitidis* e *Neisseria gonorrhoeae* (important compulsory pathogens of humane mucous membranes, the first one causing cause agent of meningitis and the second one causing gonorrhea) (Merz, A. J., and So, M. Interactions of pathogenic Neisseriae with epithelial cell membranes. Annu. Rev. Cell Dev. Biol. 16, 423-457. 2000; Pujol, C., Eugene, E., Marceau, M., e Nassif, X. 1999. The meningococcal PilT protein is required for induction of intimate attachment to epithelial cells following pilus-mediated adhesion. Proc. Natl. Acad. Sci. USA 96, 4017-4022). Other important pathogens also meke use of the motility of the "twitching" type through pilus of type IV, like *Dichelobacter nodosus*, which causes pododermatitis in bovines and *Vibrio cholerae*, na important humane pathogen, which causes cholera (J. S. Mattick. Type IV pili and twitching motility. Annu Rev Microbiol. 2002; 56:289-314. Epub 2002 Jan. 30. Review). In addition to these, *Xanthomonas axonopodis* pv *citri*, another very important bacterium for citriculture, because it causes citrus canker, also having pilus type IV (Yang, Y. C., Chou, C. P., Kuo, T. T., Lin, S. H., Yang, M. K. PilR enhances the sensitivity of *Xanthomonas axonopodis* pv. *citri* to the infection of filamentous bacteriophage Cf. Curr Microbiol. 2004 April; 48(4):251-61).

Recently, another paper by the same group that published the PilT structure of *A. aeolicus*, resolved other tree-dimensional structures of PilT protein, but of *Pseudomonas aeruginosa*, a bacterium that is phylogenetically closer to *X. fastidiosa* with respect to *A. aeolicus*. The new structures are of patial complexes, one attached to an analog of type ATP, AMP-PCP (code PDB: 3jvv) and not attached (code PDB: 3jvu), and suggested functioning mechanisms of the motor-protein that is considered the strongest biologic motor known in (A. M. Misic, K. A. Satyshur, K. T., Forest. *P. aeruginosa* PilT structures with and without nucleotide reveal a dynamic type IV pilus retraction motor. J Mol Biol. 2010 Jul. 30; 400(5):1011-21. Epub 2010 June). These structures show complexes that would be structurally closer than one believes that the PilT complexes of *X. fastidiosa* are, and point out that this is an extremely dynamic protein and has certain structural differences when attached to ADP, ATP or without ligands.

At present, important advances in the production of pharmaceuticals were achieved by computer-aided approaches. The high damages resulting from the phitopathologies that *Xylella fascidiosa* and the absence of effective solutions against this ailment stimulate us to seek new alternatives and therapeutic targets other than those used at present for combating this microorganism. Therefore, this paper describes an attempt to innovate, in the sense of carrying out new targets for structure-based drug design, in a protein not yet used for this purpose, namely PilT.

Anderson (A. C. Anderson. The process of structure-based drug design. Chem Biol. 2003 September; 1090:787-97. 2003), published a description of how one should carry out the procedure of drug design based on protein structure, from the criteria that should be adopted for choosing the therapeutic target for such a design to the development procedures, "docking" and "virtual screening". The paper discusses that the design of antimicrobial drugs should be based on targets that are essential, are found chiefly in pathogens (in opposition to non-pathogenic organisms), have a single function in the pathogen and are likely to undergo inhibition by small molecules.

The choice of PilT and, more specifically, of the residues to be used as targets, followed these recommendations. It is a protein essential to the *Xylella fastidiosa* pathogenicity. It is known that the movement via IV-type pilus is the main responsible for the dispersion of the pathogen since the inoculation point and development of the disease; it is important for other pathogens in terms of movement, formation of aggregates, adhesion and evasion of host immunologic system (J. S. Mattick. Type IV pili and twitching motility. Annu Rev Microbiol. 2002; 56:289-314. Epub 2002 Jan. 30. Review) and the residues described hereinafter, chosen as the preferred targets, have occurrence limited to the PilTs from pathogenic organisms structured with respect to the free-life organism like cyanobacteria. As already mentioned, it is known that, upon mutation of some amino acids located in the interface, the PilT ceased exerting its function and the mutated organism was not capable of moving ("Twitching motility" (K. a. Satyshur, G. A. Worzalla, L. S. Meyer, E. K. Heiniger, K. G. Aukema, A. M. Misic, and K. T. Fore. Crystal Structures of the Pilus Retraction Motor PilT Suggest Large Domain Movements and Subunit Cooperation Drive Motility. Structure 15, 363-376. March 2007). Therefore, we start from the presupposition that that the interfaces are essential to maintain the function and motility, and that the creation of a compound that is capable of attaching to this region will prevent this correct functioning and/or prevent the correct association of the monomers at the moment of forming the hexamer.

There are a number of scientifically recognized papers that have used techniques similar to those employed in this paper, aiming at a better understanding of the protein structures and/or the identification of therapeutic targets for the development of drugs. Hereinafter, one exposes a number of citations of some of these papers.

Li et al. 1996 (R. Li, X. Chen; B. Gong, P. M. Seizer, Z. Li, E. Davidson, G. Kurzban, R. E. Miller, E. O. Nuzum, J. H. McKerrow, R. J. Fletterick, S. A. Gillmor C. S. Craik, I. D. Kuntz, F. E. Cohen and G. L. Kenyon. Structure-Based Design of Parasitic Protease Inhibitors. Bioorganic & Medicinal Chemistpy 1996, 4, No. 9, 1421-1427) exploited the use of known similar protein structures, in order to develop possible candidates to drugs to be used, not only against parasites, but also against other infectious diseases and process of unknown cell multiplication. The authors further advocate that the structure-based design identifies favorable and non-favorable interactions between a potential inhibitor and a determined target.

Sheng et al. 2004 (Sheng, C., Zhang, W., Zhang, M., Song, Y., Ji, H., Zhu, J., Yao, J., Yu, J., Yang, S., Zhou, Y., Zhu, J., Lu, J. Homology Modeling of Lanosterol 14α-Demethylase of *Candida albicans* and *Aspergillus fumigatus* and Insights into the Enzyme-Substrate Interactions. J Biomol Struct Dyn. 2004; August; 22(1):91-99) present the use of a protein structure of *Mycobacterium tuberculosis* (14alpha-sterol demethylase) as template for modelling the three-dimensional lanosterol protein straucture 14alpha-demethylase of other microorganisms, in this case: *Candida albicans* and *Aspergillus fumigatus.*

Marrone et al. 1997 (T. J. Marrone, J. M. Briggs, and J. A. McCammon. STRUCTURE-BASED DRUG DESIGN: Computational Advances. Annu. Rev. Pharmacol. Toxicol. 1997 37:71-90) presented a review with the structure-based computer methods showing the use thereof to discover, refine or alter therapeutic alteration. The review cites various, such as molecular viewing, molecular modeling, modeling techniques using 3-D databanks, methods of fragmenting and disturbing the free energy.

In document WO200135316, a computational method was described for selecting drugs, based on polymorphism, which comprises obtaining more than one amino acid sequence from the target proteins that are the product of a gene exhibiting polymorphism, wherein the sequences represent different genetic polymorphisms and the generation of variations of 2-d protein structural models; computational tests of molecular drug docking with the target protein models were carried out; energetic refinement of the docked complexes; determination of the binding interaction between the drug or potential 15 new molecules candidate to drug and their respective models; selection of drug therapies based on the drug or drugs with greater binding potential/interaction with the varying structural models.

Document WO9425860 described a computational system for modeling the three-dimensional structure of a model protein, this modeling being based on the three-dimensional structure of a template protein, in the amino acid sequence of the model protein, in the proteins containing the plurality of the amino acids, in each amino acid having a main atom chain and side atom chains, in each atom in a three-dimensional structure containing a determined positioning.

In document U.S. Pat. No. 5,884,230, a computational system was described for generating a collection of information relating to the position between pairs of amino acids for use in modeling an oral three-dimensional structure of a varying region of a model protein. The computational system has information about the relative positions between pairs of amino acids of varying regions of a protein collection.

In document WO2006110064, a method was described for selecting potential medicinal compounds and drug design, which comprises predicting values of the binding affinity or of the interaction energy released from the protein-ligand interaction from a calculated score.

In document US2001000807, a computational method was described for identifying binding targets in proteins and other macromolecules. The invention includes an algorithm for predicting binding targets in proteins. In spite of requiring knowledge of the protein structure, the algorithm does not need the location, nature of the binding sites or of the ligands. The binding targets in the protein are identified and classified according to the optimum expected affinity. This invention has a significant application in designing structure-based drugs.

In document U.S. Pat. No. 5,580,723, a method was described for identifying at least one unknown active domain in a known region of amino acids sequence of a correlated polypeptide, containing similarity, of natural occurrence. The polypeptide containing the parenthood relationship should have it biological activity pre-defined. And the active domain under identification should be capable of interacting with the same target of the correlated polypeptide, in an active form, the interaction of which is responsible for its biologic activity.

In document US2005123995, a method was described with a computational design code for evaluating the release of binding energy between residues of polypeptide amino acids. In making use of the canonic sampling properties, a basis for the technology, the affinity for binding filaments in the proximities of each protein residue may be efficiently calculated. The binding volume associated to each pair of fragments-residue is estimates on the basis of yesple proximity criteria and an affinity mapping of the protein surface may be obtained thin this way. The analysis of such data for various types of fragment provides valuable information for helping to identify binding sites of the protein, as well as to identify key fragments that may be used for constructing potential drugs.

In document WO0135316 a method was described, based on drug design computation, based on genetic polymorphism. Such a method comprises obtaining more than one amino acid sequence of the target protein, generation of three-dimensional models of the protein structure and their variants, design of drug candidates, modification of drugs existing on the basis of the prediction of the molecular interaction between the models and the candidate drugs, with their respective variations.

In document US2005257285, an antimicrobial chimeric protein was described for the therapeutic and prophylactic treatment of plant diseases causes by *Xylella fastidiosa*. The antimicrobial protein is composed by a polypeptide domain of surface recognition, capable of binding to components of the bacterial membrane, fused to a polypeptide domain of bacterial lysis, capable of affecting the lysis or rupture of the bacterial membrane. Particularly, the method and composition for the treatment of Pierce's disease are provided. The method for generating the transgenic *Vitus vinefera* plant, expressing the chemeric protein in the xylem is also presented.

In document US2005053584, the introduction of a strain with lower virulence was described, defined as "benign", of *X. tastidiosa* in the plants of interest which are usually susceptible to the infectious disease caused by this pathogen. The inoculated plants are generally resistant to Pierce's disease, at least about 3-4 years. The invention further presents the bacterial "benign" strain suitable for controlling the Disease, besides providing reinforcement injections (Booster) for every 3-4 years.

In document WO2006069160, a construct was described which comprises a nucleic acid molecule coding for a type HecA recombinant hemaglutinin, or a fragment thereof, which imparts resistance to the infection by *Xylella fastidiosa* when expressed in plants.

In document MXNL06000034, an anti-*Xylella fastidiosa* substance was described, which was developed by joining an avian csFy and a Cecropin P1 (CP1) lytic peptide, which is expressed in a bacteriophase M13. This bacteriophase is capable or removing 100% of the bacterium in in-vitro cultures at a concentration of $3.6\times10^5$ phages/cell after 28 hours of incubation.

In document U.S. Pat. No. 6,548,265, a method was described for treatment and/or prophylaxis of infectious diseases caused by bacteria which adhere to the tissues through the pilus. The method is based on the interaction with periplasmatic molecular chaperones, thus interfering with the assembly of the pilus, preventing or decreasing the bacterial infection. However, this method does not include the type-IV pilus (used for twitching motility of the pathogens like *Xylella fastidiosa*), since this system does not require chaperones for the correct assembly and functioning.

In document US 2003/0176662, a procedure was described for designing structure-based drugs, from a C hepatitis protein structure. The authors did onto present any pharmaceutical structure, but suggested the targets and, on the basis of this identification, suggested the "de novo design" of the drugs that obey the phamacophore determinants found in the concentrated target in a determined amino acid of protein structure disclosed.

In document US2005/0004766, a procedure was described for use of structures obtained by homology modeling, using the polymorphic protein sequences, for designing patient-specific drugs. In this patent, one can see that the authors do not report any pharmaceutical for the modeled structures, but describe in details how to obtain the structural models and how to proceed with the identification of the targets for the rational design of drugs.

The present patent application relates to a new alternative to the present processes and researches that aim at eradicating/inactivating the photophatogenic *Xylella fastidiosa* strains. There are various successful cases of computational design of drugs, directed to structurally delimited therapeutic targets, as can be seen in the article by Villoutreix and co-workers (Villoutreix, B. O., Eudes, R., Miteva, Ma. A. Structure-based virtual screening: recent success stories. Comb Chem High Throughput Screen. December; 12(10): 1000-16). The present description of novel therapeutic targets corresponding to pharmaceuticals, carried out for interface regions of the hexameric PilT protein, is different from the techniques already presented, because this is a novel therapeutic target, unexploited so far for this purpose, the PilT protein, in a specific and little-studied region in the science of computational design of drugs (interface amino acids), which will aim at preventing the formation of the hexameric complex and/or its destabilization with concomitant inhibition of the motility of the bacterium.

SUMMARY OF THE INVENTION

The invention relates to identification of specific regions in protein PilT, so that it can be inactivated or its activity can be reduced, thus reducing or preventing the development of bacterial infection. The protein in question is related to the motility of the pathogen and is described in the literature as being essential to the development of phitopathogenies correlated to the above-mentioned pathogen. The main phitopathogenies correlated to this bacteria are Citrus Variegated Chlorosis (CVC, called also "Amarelinho") and Pierce's disease, which can attack the citrus cultivars in general and of grapevine respectively, besides other various diseases that affect other plants of economic interest. The importance of combating these diseases is pointed out for its capability of rapid zoocoric spread, having the "cigarrinha" (Hemiptera: Cicadellidae) as its main vector, and for its negative impact on the cultivars.

A method was developed for identifying therapeutic targets in residues forming interface (IFR) between the monomeric polypeptides that constitute the hexamers of PilT protein in three possible conformations (bound to ATP, ADP and without ligands), by modeling three hexameric template complexes in different conformations. The templates used for such modeling were the structure of *A. aerolicus* PilTs (herein called AaPilT) bound to ADP and two structures of *P. aeruginosa* (PaPilT) bound to ATP, and no ligand and deposited on the PDB (Protein Databank). Subsequently, one predicted residues located on the interface, their characteristics, and analysis of Computational Biology to indicate target sites for the design of drugs based on the structures generated from *Xylella fastidiosa* PilT (herein called XfPilT). Then, one proposed a detailed description of how one should carry out the computational design of drugs that will bind to the predicted target sites. As a complement of this description, one proposed a practical example with drugs which we designed on the base of determinants of binding to the identified target, in this case centered on the Glu89 amino acid, having a very strong theoretical support to design an optimum "lead", since we found the high docking index degree (it is important to point out that the scope of the invention is not limited to these designed drugs).

BRIEF DESCRIPTION OF THE FIGURES

FIG. 1*a* is a structural overlapping of the *X. fastidiosa* (Xf) Pilt model, called XfAa1 (in gray), created from the hexamer of PIlT of the *A. aerolicus* (Aa) bacteria (in its conformation bound to ADP), the code of which PDB is 2gsz (in black). FIG. 1*b* is a structural overlapping of the Xf PilT model, called XfPa1 (in gray), created on the basis of the hexamer generated from the biological unit of the PDB (3jvu) of *P. Aeruginosa* (Pa) PilT in its conformation without ligands (in black). FIG. 1*c* is a structural overlapping of the Xf PilT called XfPa2 (in gray), created on the basis of the hexamer generated from the biological unit of the PDB (3jvv) of Pa PilT in its conformation bound to an analog of the ATP (AMP-PCP) (in black). The RMSD vectors are represented.

DETAILED DESCRIPTION OF THE INVENTION

Figure 1:
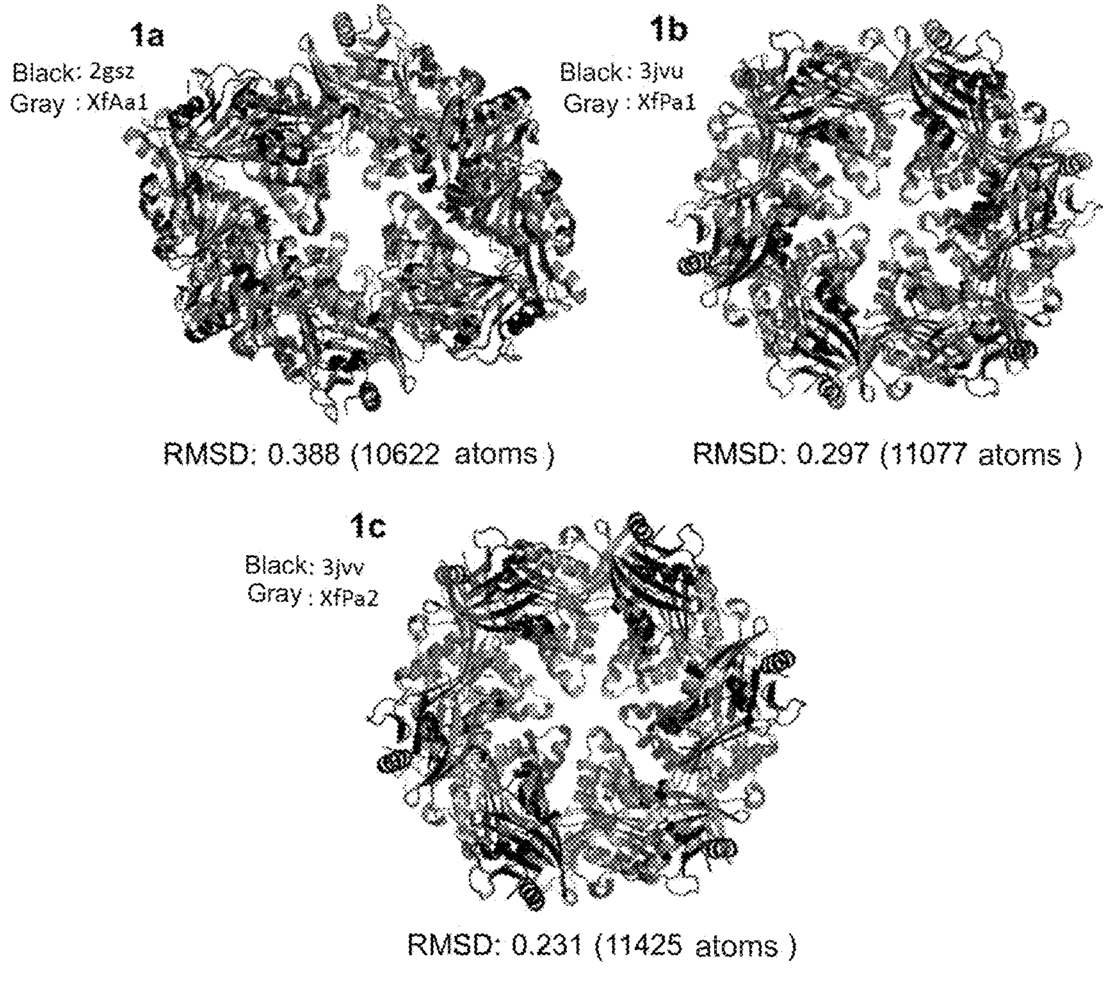
FIG. 1 is a representation of structural alignment of the cited model hexamers and the created templates used as a basis for modeling them by homology.

The present invention relates to a method for identifying regions likely to be used as therapeutic targets for computational design of drugs, based on structures existing on the surface of monomers constituting the PilT protein, as well as the listing and characterization of the target predicted, with a view to design molecules that bind in these regions and that are potentially applicable in impairing the activity of this protein, thus controlling infectious processes.

The proposed method consists of the following steps:

1—If the complex of the protein of interest, for any reason, is not described or its structure is undetermined, one should generate a model from another protein with high similarigy in its primary sequence, by using homology modeling through the program Swiss-Model (Guex, N. and Peitsch, M. C. 1997. SWISS-MODEL and the Swiss-PdbViewer: An environment for comparative protein modeling. Electrophoresis 18:2714-2723) or the program Modeller (Eswar, N., Marti-Renom, M. A., Webb, B., Madhusudhan, M. S., Eramian, D., Shen, M., Pieper, U., Sali., A. 2006. Comparative Protein Structure Modeling With MODELLER. Current Protocols in Bioinformatics, John Wiley & Sons, Inc., Supplement 15, 5.6.1-5.6.30). The validation of the modeling is then carried out through the analysis of the Ramachandran graphs (Ramachandran, G. N., Ramarkrishnan, C., Sasisekharan, V. 1963. Stereochemistry of polypeptide chain conformations. J. Mol Biol 7:95-99) and the use of the ProSA web-service (Whiederstein, M., Sippl, M. J. 2007. ProSA-web: interactive web service for the recognition of errors in three-dimensional structures of proteins. Nucleic Acid Research, Web Server issue: W407-10).

2—Use of the program Deep-View for generating the PDB file of the complex of the protein of interest, by structural overlapping with the complex used as template by the modeling and minimizing energy by using the program Gromacs (Van Der Spoel, D., Lindahl, E., Hess, B., Groenhof, G., Mark, A. E., Berendsen, H. J. 2005. "GROMACS: fast, flexible, and free". J Comput Chem 26 (16): 1701-18. doi:10.1002/jcc.20291.);

3—Use of the server STING (Neshich, G., Togawa, R., Mancini, A. L., Kuser, P. R., Yamagishi, M. E. B., Pappas Jr., G., Torres, W. V., Campos, T. F., Ferreira, L. L., Luna, F. M., Oliveira, A. G., Miura, R. T., Inoue, M. K., Horita, L. G., de Souza, D. F., Dominiquini, F., Alvaro, A., Lima, C. S., Ogawa, F. O., Gomes, B. G., Palandrani, J. C. F., dos Santos, G. F., de Freitas, E. M., Mattiuz, A. R., Costa, I. C., de Almeida, C. L., Souza, S., Baudet, C. and Higa, R. H. 2003. STING Millennium: a Web based suite of programs for comprehensive and yesultaneous analysis of protein structure and sequence. Nucleic Acids Research, 31:13, 3386-3392) for generating the file TGZ containing all the physicochemical and structural parameters of the STING_DB.

4—All the parameters generated STING are charged in the Star STING (Neshich, G., Mazoni, I., Oliveira, S. R., Yamagishi, M. E., Kuser-Falcão, P. R., Borro, L. C., Morita, D. U., Souza, K. R., Almeida, G. V., Rodrigues, D. N., Jardine, J. G., Togawa, R. C., Mancini, A. L., Higa, R. H., Cruz, S. A., Vieira, F. D., Santos, E. H., Melo, R. C., Santoro, M. M. The Star STING server: a multiplatform environment for protein structure analysis. Genet Mol Res. 2006 Dec. 1; 5(4):717-22) and in the Java Protein Dossier (Neshich, G., Rocchia, W., Mancini, A. L., Yamagishi, M. E., Kuser, P. R., Fileto, R., Baudet, C., Pinto, I. P., Montagner, A. J., Palandrani, J. F., Krauchenco, J. N., Torres, R. C., Souza, S., Togawa, R. C., Higa, R. H. 2004. JavaProtein Dossier: a novel web-based data visualization tool for comprehensive analysis of protein structure. Nucleic Acids Res. 2004 Jul. 1; 32 (Web Server issue):W595-601), a platform for detailing and integrating the analysis of structural function.

5—Identification of the interface forming residues (IRFs) and obtainment of the data of the respective areas by using the program SurfV (Sridharan, S., Nicholls, A. and Honig, B. 1992. A new vertex algorithm to calculate solvent accessible surface areas. Biophys. J., 61, A174) to calculate the area of accessibility to the solvent by residues in two sceneries: for the isolated chain and for the chain in the complex with other chains.

6—Studying the occurrence of categories of amino acids in Interface Forming Residues (IFRI) and free Surface (which is given by the difference between the total molecular surface), with regard to the amino acids that form it, and also as far as the categories of amino acids are concerned: Polares: Cys, Ser, Thr, Tyr, Asn, Gln, His and Trp; Carregados: Asp, Glu, Arg, Lys; Hidrofóbicos: Ala, Ile, Leu, Val, Met, Phe and Pro; and Glicina: which can be considered fourth category (Branden, C. and Tooze, J. 1991. Introduction to protein structure. Garland Publishing, New York, ISBN 0-815-30270-3). This phase is important for indicating to which extent the interface in question is polar and charged. The analysis if made by using MySQL databanks (http://www.mysql.com/) and tables containing area values obtained with the program Surf V.

7—Use of the STING (Neshich, G., Togawa, R., Mancini, A. L., Kuser, P. R., Yamagishi, M. E. B., Pappas Jr., G., Torres, W. V., Campos, T. F., Ferreira, L. L., Luna, F. M., Oliveira, A. G., Miura, R. T., Inoue, M. K., Horita, L. G., de Souza, D. F., Dominiquini, F., Alvaro, A., Lima, C. S., Ogawa, F. O., Gomes, B. G., Palandrani, J. C. F., dos Santos, G. F., de Freitas, E. M., Mattiuz, A. R., Costa, I. C., de Almeida, C. L., Souza, S., Baudet, C. and Higa, R. H. 2003. STING Millennium: a Web based suite of programs for comprehensive and yesultaneous analysis of protein structure and sequence. Nucleic Acids Research, 31:13, 3386-3392) and of the Java Protein Dossier (Neshich G., Rocchia W., Mancini A. L., Yamagishi M. E., Kuser P. R., Fileto R., Baudet C., Pinto I. P., Montagner A. J., Palandrani J. F., Krauchenco J. N., Torres R. C., Souza S., Togawa R. C., Higa R. H. 2004. JavaProtein Dossier: a novel web-based data visualization tool for comprehensive analysis of protein structure. Nucleic Acids Res. 2004 Jul. 1; 32 (Web Server issue):W595-601) for calculating the number, type and, therefore, the total energy of the contacts established between the interface of the amino acids of selected chain and adjacent chains.

8—Once in possession of the data describing the area occupied by specific residues in a determined surface, carrying out the creation of two indexes: Interface Contacts Energy Density (ICED), which is given by the sum of the energies for all the contacts IFRs divided by the sum of the area occupied in the interface by all the IFRs; and Interface Contacts Density (ICD) that is given by the total number of contacts established through each contact divided by the total area. Additionally, the program Java Protein Dossier (Neshich, G., Rocchia, W., Mancini, A. L., Yamagishi, M. E., Kuser, P. R., Fileto, R., Baudet, C., Pinto, I. P., Montagner, A. J., Palandrani, J. F., Krauchenco, J. N., Torres, R. C., Souza, S., Togawa, R. C., Higa, R. H. 2004. JavaProtein Dossier: a novel web-based data visualization tool for comprehensive analysis of protein structure. Nucleic Acids Res. 2004 Jul. 1; 32 (Web Server issue):W595-601) is used for general structural analysis and the program PyMol (Delano, W. L. 2002. The PyMOL Molecular Graphics System Delano Scientific, San Carlos, Calif., USA. http://www.pymol.org) is used for generating the molecular images.

9—Carrying out the selection of therapeutic targets on the basis of physicochemical and structural characteristics (such as: high contact energy values, polarity) (area exposed to the solvent, presence in "pocket", among others of interest, by using the module Select of the STING Java Protein Dossier (Neshich, G., Rocchia W., Mancini, A. L., Yamagishi, M. E., Kuser, P. R., Fileto, R., Baudet, C., Pinto, I. P., Montagner, A. J., Palandrani, J. F., Krauchenco, J. N., Torres, R. C., Souza, S., Togawa, R. C., Higa, R. H. 2004. JavaProtein Dossier: a novel web-based data visualization tool for comprehensive analysis of protein structure. Nucleic Acids Res. 2004 Jul. 1; 32 (Web Server issue):W595-601).

10—Alignment between the primary structure of proteins homologous to the protein of interest through the program ClustalW 2.0 (Larkin, M. A., Blackshields, G., Brown, N. P., Chenna, R., McGettigan, P. A., McWillian, H., Valentin, F., Wallace, I. M., Wilm, A., Lopez, R., Thompson, J., D., Gibson, T. J., Higgins, D. G. 2007. Clustal W and Clustal X version 2.0. Bioinformatics, 23, 2947-2948) evidencing the similarities and differences between these two sets of proteins and seeking correspondences in the alignment of primary structure of the residues contacted in "9". Following certain criteria like: presence exclusively in the pathogenic bacteria sequences, choosing the preferred therapeutic targets.

11—Proceeding with industrial methods and protocols for structure-based drug design, regardless of whether it is a novel method or one based on structures already known by virtual screening.

EXAMPLES

The invention will now be described in greater detail with reference to the following examples, which should not be taken as limiting the scope of the invention.

In order to understand better the physicochemical characteristics of the *Xylella fastidiosa* PilT, which are believed to be the key to the correct functioning of the protein and since the *Xylella fastidiosa* PilT has a high similarity in primary sequence with respect to *A. aeolicus* PilT (about 68% similarity and 49% identical amino acids) and even higher with respect to *P. aeruginosa* PilT (about 87% similarity and 74% identical amino acids, as indicated by the probram BLASTp (S. F. Altschul, T. L. Madden, A. A. Schäffer, Z. Zhang, W. Miller, D. J. Lipman. 1997. Gapped BLAST and PSI-BLAST: a new generation of protein database search programs. Nucleic Acid Res. 1997 Sep. 1; 25(17):3389-402), one used 3-D structures of the PilT hexamers *Aquifex aeolicus* (Aa) (PDB code: 2gsz, in a conformation bound to ADP obtained ftp://ftp.wwpdb.org/pub/pdb/data/structures/all/pdb/pdb2gsz.ent.gz) and the *Pseudomonas aeruginosa* (Pa) PilTs hexameric complexes (PDB codes: 3jvu and 3jvv, in unbound conformations and conformations bount to ATP, respectively, obtained in the addresses ftp://ftp.wwpdb.org/pub/pdb/data/biounit/coordinates/all/3jvu.pdb1.gz and ftp://ftp.wwpdb.org/pub/pdb/data/biounit/coordinates/all/3jvv.pdb1.gz) for homology modeling of each of the 6 chains different from *X. fastidiosa* PilT (XfPilT) on the basis of the corresponding chains in the templates, and in the three conformations, based on 2gsz, 3jvu and 3jvv, using the program Modeller (Eswar, N., Marti-Renom, M. A., Webb, B., Madhusudhan, M. S., Eramian, D., Shen, M., Pieper, U., Sali., A. 2006. Comparative Protein Structure Modeling With MODELLER. Current Protocols in Bioinformatics, John Wiley & Sons, Inc., Supplement 15, 5.6.1-5.6.30), generating, in all, 18 chains, of 3 complexes.

Subsequently, by using the program Deep-View (Guex, N. and Peitsch, M. C. 1997. SWISS-MODEL and the Swiss-Pdb-Viewer: An environment for comparative protein modeling. Electrophoresis 18:2714-2723), one carried out the assembly of the complexes on the basis of structural overlapping of the XfPilT chains in their templates. In this way, three files PDB were created for the XfPilT hexamers: one based on 2gsz, another based on 3jvu and the other based on 3jvv. The making of these three templates of complexes is of great importance, since it aims at simulating the various states of the PilT protein, which is exactly dynamic and probably mute from conformation to conformation for the correct functioning and rupture of the ATP in ADP. The existence of these different conformations in the templates enable one to suggest targets that are exposed in a conformation and/or chain and inside the surface in another, as interesting targets for preventing the correct function of the protein when the latter is already assembled on the basis of the pilus. Therefore, it is necessary to study the three conformations and seek similarities and differences between them *Pseudomonas aeruginosa* (Pa).

After assembling the complexes, one carried out minimization of the energy by using the program Gromacs (Van Der Spoel, D., Lindahl, E., Hess, B., Groenhof, G., Mark, A. E., Berendsen, H. J. 2005. "GROMACS: fast, flexible, and free". J Comput Chem 26 (16): 1701-18. doi:10.1002/jcc.20291). The three minimized complexes generated were called XfAa1, XfPa1 and XfPa1, and are listed in table 1. An evaluation was made Fo the modeled complexed using the analysis of Ramachandran graphs (Ramachandran, G. N., Ramarkrishnan, C., Sasisekharan, V. 1963. Stereochemistry of polypeptide chain conformations. J. Mol Biol 7:95-99), which indicated that the three templates had more than 98% of the residues in the permitted regions. The evaluation through the ProsaWeb indicated that the z-score values ranged from −8.96 to −9.67, values that are contained in the interval of results usually encountered for the native proteins of similar size (Whiederstein, M., Sippl, M. J. 2007. ProSA-web: interactive web service for the recognition of errors in three-dimensional structures of proteins. Nucleic Acid Research, Web Server issue: W407-10). Therefore, the three templates of XfPilT complexes were considered acceptable for continuation of the analysis.

TABLE 1

Identification of the three templates created, on which the homology modeling, description and values obtained for evaluation of the templates were based.

| Models of hexamer of Xf PilT generated | Templates used in homology modeling | Description |
|---|---|---|
| Xfa1.pdb | 2gsz.pdb | Model created by using the Modeller on the basis of the hexameric AaPilT bound to ADP (PDB; 2gsz), with additional minimization of energy carried out with the program Gromacs |
| Xfa1.pdb | 2gsz.pdb | Model created by using the Modeller on the basis of the PaPilT hexamer without ligands (PDB; 3jvu), with additional minimization of energy carried out with the program Gromacs |
| Xfa1.pdb | 2gsz.pdb | Model created by using the Modeller on the basis of the PaPilT bound to an analog of ATP (AMP-PCP) (PDB: 3jvv), with additional minimization of energy carried out with the program Gromacs |

The modeled structures of thee *X. fastidiosa* (XfAa1, XfPa1e XfPa2) PilT hexamers were structurally aligned against their templates (AaPilT com ADP: 2gsz, PaPilT without ligands: 3jvu and PaPilT with ATP: 3jvv), as shown in FIG. 1, which resulted in overlapping with deviations of 0.388, 0.297 and 0.231 for the three alignments respectively shown in 1*a*, 1*b* and 1*c*, which indicates that the structures of the complexes are very similar to each other (template vs. the model generated).

By using the platform Blue Star STING (Neshich, G., Togawa, R., Mancini, A. L., Kuser, P. R., Yamagishi, M. E. B., Pappas Jr., G., Torres, W. V., Campos, T. F., Ferreira, L. L., Luna, F. M., Oliveira, A. G., Miura, R. T., Inoue, M. K., Horita, L. G., de Souza, D. F., Dominiquini, F., Alvaro, A., Lima, C. S., Ogawa, F. O., Gomes, B. G., Palandrani, J. C. F., dos Santos, G. F., de Freitas, E. M., Mattiuz, A. R., Costa, I. C., de Almeida, C. L., Souza, S., Baudet, C. and Higa, R. H. 2003. STING Millennium: a Web based suite of programs for comprehensive and yesultaneous analysis of protein structure and sequence. Nucleic Acids Research, 31:13, 3386-3392) and the program Java Protein Dossier (JPD) (Neshich, G., Rocchia, W., Mancini, A. L., Yamagishi, M. E., Kuser, P. R., Fileto, R., Baudet, C., Pinto, I. P., Montagner, A. J., Palandrani J. F., Krauchenco, J. N., Torres, R. C., Souza, S., Togawa, R. C., Higa, R. H. 2004. JavaProtein Dossier: a novel web-based data visualization tool for comprehensive analysis of protein structure. Nucleic Acids Res. 2004 Jul. 1; 32 (Web Server issue):W595-601), chiefly in the module called "Formiga" (ant) (Higa, R. H.; Neshich, G. Defining 3D residue environment in protein structures using SCORPION and FORMIGA. Bioinformatics (Oxford), Oxford, v. 20, n. 12, p. 1989-1991, 2004), it was possible to select and analyze the interface forming residues as well as find out the area values that these occupy in the Interface and in the free Surface, and such data are not calculated through the program SurfV (Sridharan, S., Nicholls, A. and Honig, B. 1992. A new vertex algorithm to calculate solvent accessible surface areas. Biophys. J, 61, A174).

Figure 2:
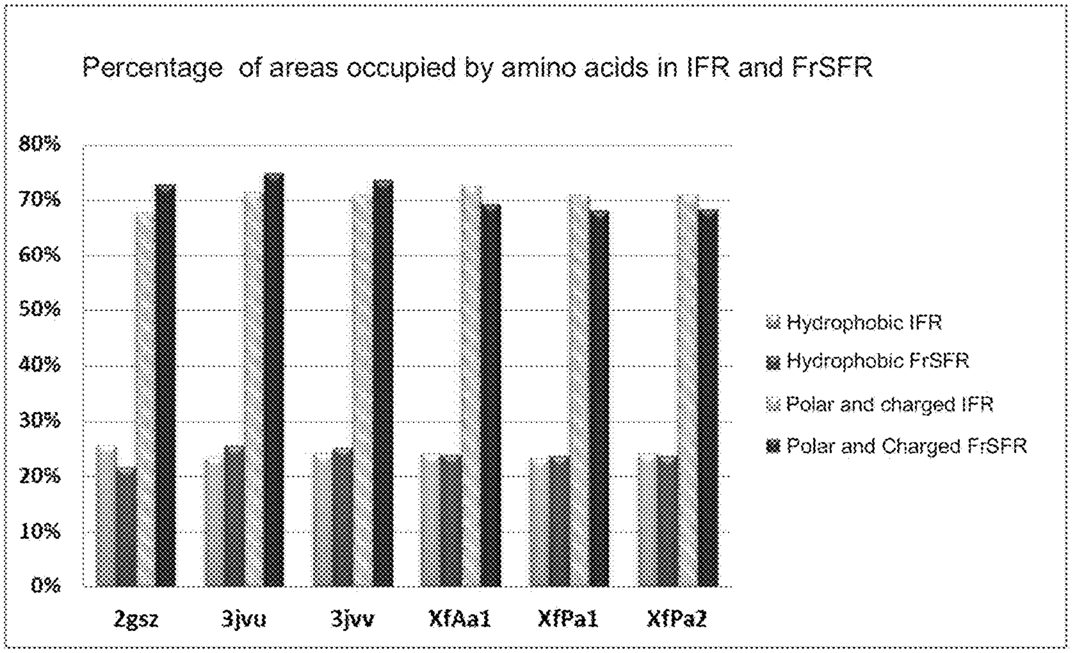
FIG. 2 shows percent vectors of average occupation of area in the interface and free surface of the hexamers by two categories of amino acids (hydrophobic and polar+carried). The structures represented in this figure are: those used as template (from left to right: 2gsz (AaPilT in conformation of binding to ADP), 3jvu (PaPilT, unbound conformation), 3jvv (PaPilT), conformation bound to ATP), XfAa1 (XfPilT model based on 2gsz), XfPa1 (XfPilT model based on 3jvu) and XfPa2 (XfPilT model based on 3Jvvu).

With this analysis, it was possible to observe that the nature of the Interface Forming Residues (IFR) of the *Xylella fastidiosa* PilT complexes, is predominantly of polar charged residues, as can be seen in FIG. 2, similar to the results obtained by Satyshur and co-workers (Satyshur K. Aa., Worzalla G. A., Meyer L. S., Heiniger E. K., Aukema K. G., Misic A. M., Forest K. T. 2007. Crystal structures of the pilus retraction motor PilT suggest large domain movements and subunit cooperation drive motility. Structure. 2007 March; 15(3):363-76) which indicate that the interfaces would be predominantly charged and polar. The sum of all the interface areas of all the monomers of the *Aquifex aeolicus* PilT hexamer 18890.20 $Å^2$, of which 13455.55 $Å^2$ (71.23%) are formed by polar and charged residues of the categories. For *X. fastidiosa*, PilT hexamers there are 18173.88 $Å^2$, 18446.96 $Å^2$ and 18882.558 $Å^2$ of total interface areas and 13592.32 $Å^2$ (72.5%), 14020.77 $Å^2$ (70.88%) and 14208.91 $Å^2$ (70.88%) of areas occupied by polar and charged residues, respectively for XfAa1, XfPa1 and XfPa2, which demonstrates clearly the importance that such residues have in the constitution of the IFRs. The interfaces of the Pa hexamers have values of area occupied by polar and charged amino acids similar that found for Xf: 71.42% and 70.93% for 3jvu and 3jvv, respectively.

Statistic approaches were used to find whether the values of the averages of the percents of areas occupied by polar and charged residues were significantly different from those found for the chains of Pa and Xf PilT hexamers with respect to Aa hexamer. It was observed that such data are highly likely to follow a normal distribution (P-value of the test for D'Agostino normality=0.092) and Student T Test, which resulted in a P value ($5.25\times10^{-6}$), which demonstrated that the interfaces of Aa (2gsz) PilT interfaces are highly likely to be significantly different from the averages found for the PilT interfaces of the Pa and Xf pathogenic proteobacteria. It was thus suggested that the 2gsz interfaces have a smaller area occupied by such residues if compared with the Pa and Xf PilT interfaces. It was also checked through the T text, whether the values of areas occupied by polar and charged residues were similar to those found in the interfaces of the models with respect to the templates used for modeling them. In the comparison of 3jvu (Pa PilT hexamer without ligands) against XfPa1 and of 3jvu (Pa PilT hexamer bound to AMP-PCP) against XfPa2 resulted in P-values equivalent to 0.96 and 0.89, respectively, indicating that there is a high probability that they refer to similar data, which in this case suggest that the Pa and Xf PilT interfaces are equally occupied, in their majority, by polar and charged residues. In the comparison of XfAa1 with the template used for modeling, 2gsz (Aa PilT hexamer), a P-value of 0.019 was obtained, which indicates that these are different samples, suggesting that Aa PilT has a different area of occupation by such residues with respect to Xf PilTs. These results can suggest that the interfaces of the pathogenic proteobacteria are more polar and charged that those of other distant bacteria such as Aa. This characteristic is of the utmost importance, since the presence of various residues capable of establishing contact of electrostatic nature and other polar contacts such as hydrogen bridges indicates that various sites among these may be used to identify a target for the structure-based drug design (A. C. Anderson. The process of structure-based drug design. Chem Biol. 2003 September; 10(9):787-97).

These results can indicate an important characteristic of the Pa and Xf PilTs: their interfaces seem to have a slightly larger area occupied by residues that are capable of forming interactions or strong contact (for instance: of attractive/repulsive electrostatic nature and hydrogen bridges), with respect to the Aa, 2gsz PilT complex. Complementarily, the *A. aeolicus* PilT interfaces have slightly hydrophobic area than the *X. fastidiosa* PilT interfaces, which can indicate a greater inclination of the IFRs of *A. aeolicus* 2gsz to form high-energy contact. A way to test this latter hypothesis is by analyzing the number, type and energy of contact established between the IFRs of both hexamers. By using the program STING JPD, one can identify which IFRs were establishing contacts through the given interfaces. It was observed that many hydrophilic amino acids are identified by establishing contact between the *X. fastidiosa* PilT interfaces.

By using the programs Blue Star Sting and JPD, one collected data on the number, type and energies of contacts established in the interface. For area values that are approximately similar to Xf and AaPilT, the average of the sum of all the IFR contact energies to the three complexes of the *X. fastidiosa* PilT (7.008.53 $Kcal\cdot mol^{-1}$, with standard error of the average (SEM of 190.55) is higher than the corresponding value for the sum of the contact energies in the *A. aeolicus* PilT interfaces (5.203.60 $Kcal\cdot mol^{-1}$). With regard to the number of contacts established by IFRs, the interface of the *A. aeolicus* PilT establishes a total of 884 contacts, while the interfaces of the models of *X. fastidiosa* PilT have, on an average, a surprising greater number: 1.218 contacts (SEM of 12.86). The same thing is observed for the interfaces of the Pa PilTs: 1023 contacts (SEM of 74), which establishes about 6.487.40 $Kcal\cdot mol^{-1}$ (SEM of 175.80) of interaction energies, on an average, for the whole complex.

As to the charged contacts of attractive force, charged with repulsive force and hydrogen bonds (non-hydrophobic/energetically stronger contacts) established between the IFRs, the *X. fastidiosa* and *P. aeruginosa* interfaces demonstrate to have contact in larger number and with higher energy than those established in the *A. aeolicus* PilT interface. Whereas AaPIlT (2gsz) has, on an average, 88 of these contacts per chain and an average of 824.87 Kcal·mol−1 of contact energy per chain, the Xf (XfAa1, XfPa1 and XfPa2) PilTs have, respectively: an average of 115, 133 and 134 non-hydrophobic contacts per chain, which generate interaction energy in the interface of 1.044.8, 1.143.4 and 1.157.47 $Kcal\cdot mol^{-1}$. The same values for the Pa PilTs are similar to those of the Xf PilTs: number of non-hydrophobic contacts of 126 and 119 and energies of 10.74.13 and 1.018.93 Kcal·mol−1, on an average, per chain of the 3jvu and 3jvv hexamers. This indicates that the interfaces of the PilT hexamers of the Xf and Pa pathogenic proteobacteria, regardless of the conformation, establish a larger number of high-energy contacts than the interfaces of 2gsz.

Figure 3:
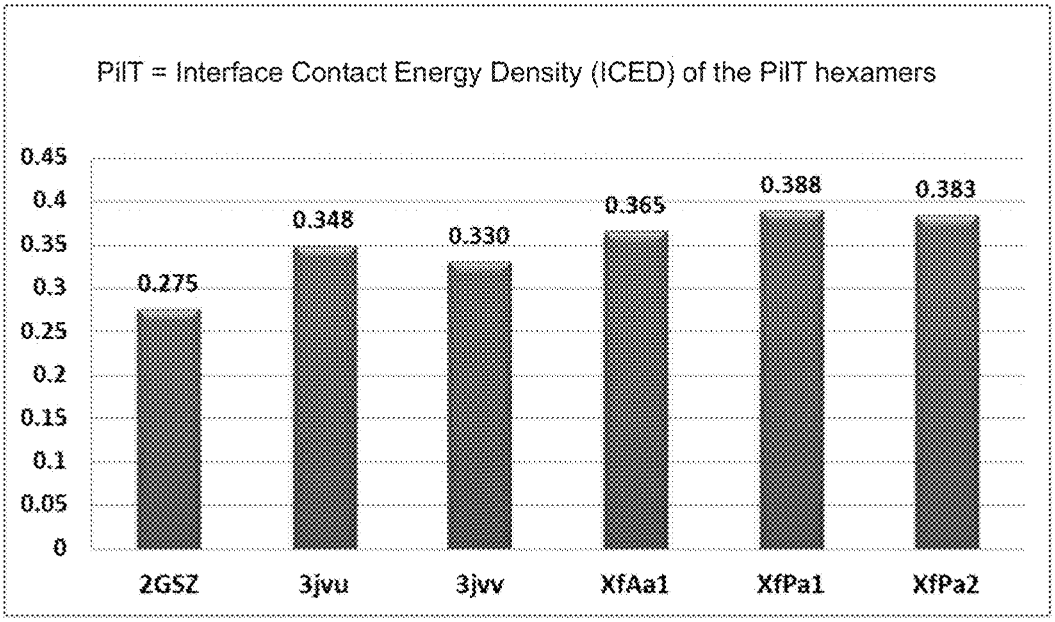
FIG. 3: 3*a* interface contact density (ICD) per complex: the total number of contacts of all the interfaces established in each hemameric complex, divided by the sum of the interface area of the whole hexamer to AaPilT 2gsz, PaPilT 3jvu, PaPilT 3jvv, XfAa1, XfPa1 and XfPa2. 3*b* shows interface contact energy density (ICD) per complex: sum of the energies of interface contacts established in each complex, divided by the sum of the interface areas of the whole hexamer to AaPilT 2gsz, PaPilT 3jvu, PaPilT 3jvv, XfAa1, XfPa1 and XfPa2.

The data obtained were used for calculating the Interface Contact Energy Density (ICED), which is an index that can illustrate the energy indexes of contacts established between all the chains of the 820 hexamers normalized by the sum of the total interface area occupied by the residues that establish these contacts. The structures of the *X. fastidiosa* and *P. aeruginosa* PilTs have higher ICEDs than *A. aeolicus* PilT, which suggests that the interfaces of the PilTs of these organisms establish more contacts and with higher energy per area with respect to what is observed for Aa PilT. The values for Xf PilTs are still higher than those of Pa PilT, as can be seen in FIG. 3. The average of the ICEDs for Aa PilT, 2gsz is of 0.28 Kcal·mol−1·$Å^{-2}$, while for the Xf and Pa PilTs they are, respectively, of 0.38 and 0.34 Kcal·mol−1·$Å^{-2}$.

In order to reply to the question whether the difference between the ICEDs and the PilTs of bacteria Xf, Pa with respect to Aa, one used the Student T Test. It was observed that the ICED data is highly likely to follow a normal distribution (P-value of the D'Agsotino normality test=0.061) and have similar standard diversions of values. Thus, one obtained a P-value equivalent to $3.48\times10^{-7}$ for the test that compared the averages of the ICED values of the Aa (2gsz) PilT with those of the Pa and Xf PilTs. This value indicates that there is a high probability that these are statistically different samples, and what they can suggest is that the interfaces of the PilT hexamers of the pathogenic proteobacteria have higher contact energies per area than the Aa PilT hexamer.

Finally, other analysis of the interface contacts were carried out: the program Blue Star STING JPD was used to view and select the amino acids that establish the energetically richer contacts (herein we put as a cut value for the selection thereof by established at least 10 Kcal·mol01 of contact energy in the interface), which had a minimum area of exposure to the solvent when in complex (in these cases, in the hexameric form), which have the characteristic of establishing hydrogen bridges and/or contacts of electrostatic nature and that are not necessarily located in pockets in complex and/or in isolation. This search resulted in 54 adjacent different residues (42 of which are part of the pockets) adjacent in complex or in isolation), which are probably the most likely to be used as therapeutic targets for structure-based drug design, as is discussed in the Paper by Anderson (A. C. Anderson. The process of structure-based drug design. Chem Biol. 2003 September; 10(9)787-97.2003). The listing of these residues, as well as some of their characteristics, such as: number of Xf PilT chains containing them, following such parameters, maximum and average values of contact energy which the residue establishes in the interface and presence of pockets, are shown in table 2.

Figure 5A:
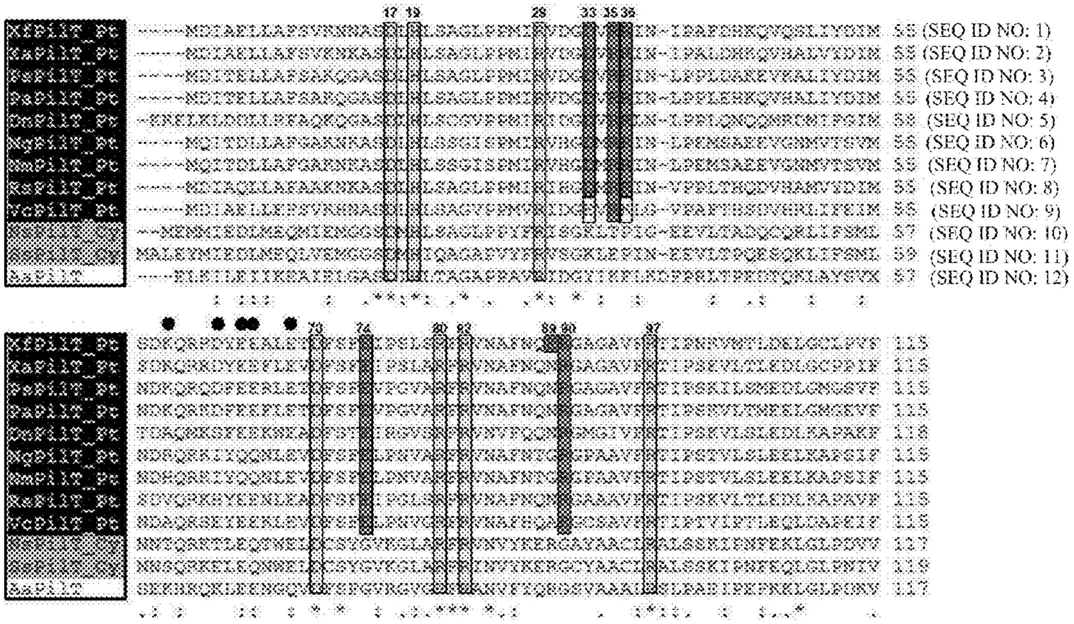
FIG. 5: alignment of the primary sequence, carried out by means of the software ClustalW (Larkin, M. A., Blackshields, G., Brown, N. P., Chenna, R., McGettigan, P. A., McWillian, H., Valentin, F., Wallace, I. M., Wilm, A., Lopez, R., Thompson, J., D., Gibson, T. J., Higgins, D. G. 2007. Clustal W and Clustal X version 2.0. Bioinformatics, 23, 2947-2948), of PilTs of Proteobacteria pathogenic bacteria that make use of movement guided by IV-type pilus (or as in the case of *Xanthomonas axonopodis*, has the IV-type pilus), as cited in "Estado da Técnica" (*Xylella fastidiosa* (XfPilT_Pt), *Xanthomonas axonopodis* pv *citri* (XaPilT_Pt), *Pseudomonas syringae* pv *tabaci* (PsPilT_Pt), *Pseudomonas aeruginosa* (PaPilT_Pt), *Ralstonia solanacearum* (RsPilT_Pt), *Vibrio cholerae* (VcPilT_Pt), *Dichelobacter nodosus* (DnPilT_Pt), *Neisseria gonorrhoeae* (NgPilT_Pt) and *Neisseria meningitidis* (NmPilT_Pt), free-life bacteria essential to keeping the balance of numberless echosystems such as Cianobacteria (*Nostoc* sp. NsPilT_Cy and *Synechocystis* sp. (SsPilT_Cy) and the bacterium of the filus Aquificales, *Aquifex aeolicus* (AaPilT). The GI identifiers of the sequences are described in the preceding paragraph. Codes of the pathogenic Proteobacteria PilTss are highlighted in black, Cianobacteria in gray. *A. aeolicus* marked in white. The most important residues in the interface, suggested as targets (which are present on at least one chain of the hexameric Xf_PilT models, with at least 10 kcal/mol of energy of interface contacts, more than 1 $Å^2$ of area exposed to the solvent when in complex, which have the characteristic of being capable of establishing hydrogen bridges and/or contacts of electrostatic nature and present or not in pockets) are highlighted as follows: the residues highlighted in long bars in Gray are possible targets that occur in all the PilTs of all the organisms used in the alignment of primary sequence; the residues highlighted in bars in dark gray with length equal to that of the bar of identifiers of pathogenic proteotacteria are the possible specific target of this category of microorganisms and that may be interpreted as preferred targets for the design of drugs to combat these pathogens in common; A small bars in dark gray represents the possible targets that occur only on *Xylella fastidiosa* PilT, these being interpreted as sole targets to Xf; the transparent small bar shows targets that vary in terms of amino acid (e.g: D33 to E33), but the exchanged amino acid has tem similar properties, considered to be a "Positive" because it indicates replacements in which the BLOSUM-62 matrix scores positively according to Altshul and co-workers (S. F. Altschul, T. L. Madden, A. A. Schäffer, Z. Zhang, W. Miller, D. J. Lipman. 1997. Gapped BLAST and PSI-BLAST: a new generation of protein database search programs. Nucleic Acid Res. 1997 Sep. 1; 25(17):3389-402.); the black circles represent the residues that have varied distribution between the organisms, which are the residues whose fields are in which in Table 2.
Figure 5B:
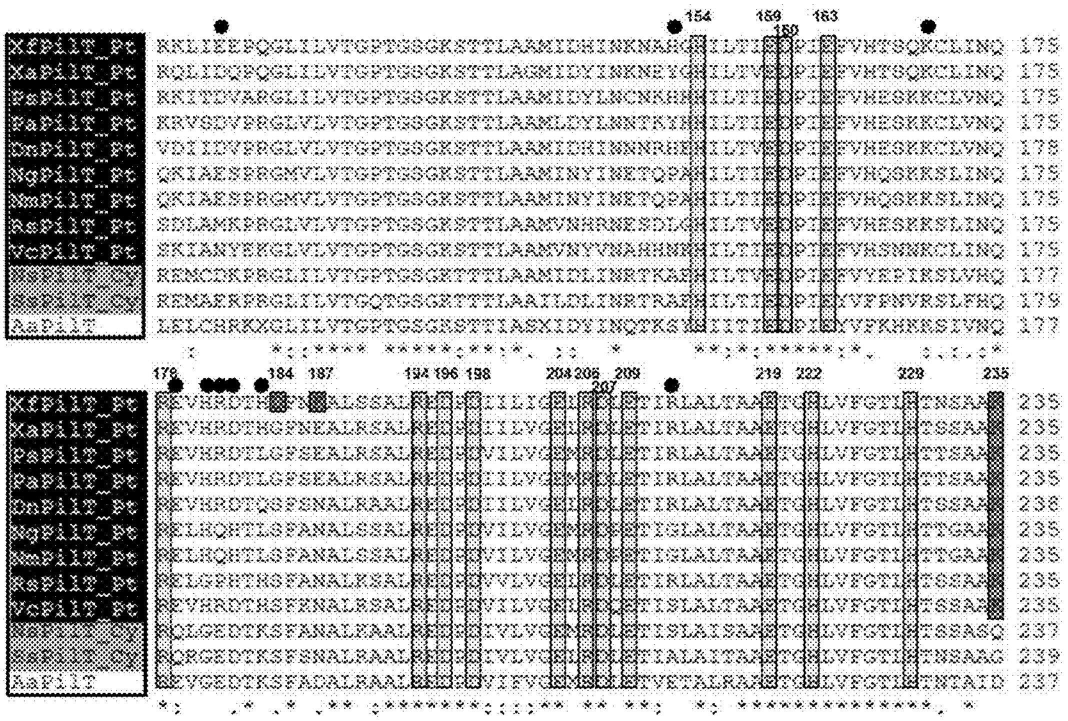
Figure 5C:
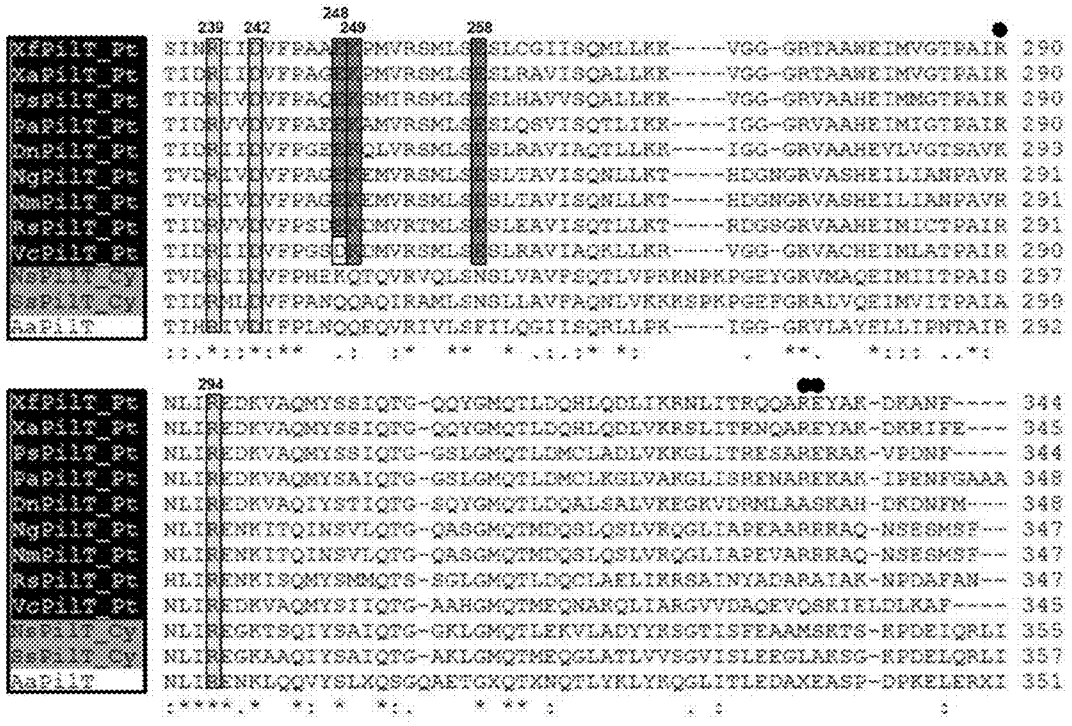

Table 2—Listing of the 54 residues identified as possible therapeutic target for the process of structure-based drug design and important information on them, such as the number of chains of hexameric XfPilT models in which the residue appears as a target, the maximum and average value of interface contact energy found for it, presence of pocket in isolation (when the chain is isolated from the remaining complex, that is when it is in its monomeric state) and in complex (that is, if in the hexameric formation there is some adjacent pocket). The last column refers to the alignment of primary sequence shown in FIG. 5, with respect to presence/absence in three groups of organisms; pathogenic proteobacteria for animals and plants (Pt), Aquificae and Cyanobacteria (CY). The sequence used in making this alignment were extracted from the Protein database of the NCBI (http://www.ncbi.nlm.nih.gov/protein/). The pathogenic proteobacteria sequences are the following: *Xylella fastidiosa* PilT 9 a 5*c* with GI:15838234 (Xf), *Xanthomonas axonoodis* pv *citri* str. 306 GI:21243651 (Xa), *Pseudomonas syringae* pv *tabaci* ATCC 11528 GI:257483590 (Ps), *Pseudomonas aeruginosa* GI: 301015820 (Pa), *Ralstonia solanacearum* UW551 GI: 83747263 (Rs), *Vibrio cholerae* V52 GI: 121728590 (Vc), *Dichelobacter nodosus* VCS1703A GI: 146329541 (Dn), *Neisseria gonorrhoeae* DGI18 GI: 240013043 (Ng), *Neisseria meningitidis* Z2491 GI: 218767246 (Nm). The Cyanobacterium PilT sequences are: *Nostoc* sp. PCC 7120 GI: 17229935 (Ns) and *Synechocystis* sp. PCC 6803 GI: 16331158 (Ss). The sequence of *Aquifex aeolicus* VF5 (Aa) used was GI: 119389376.

| Identification of the residue (amino acid and position) | Number of chains of XfPilT complexes in which the residue appears as a target | Maximum value of interface contact energy for the residue | Average value of interface contact energy for the residue | Presence in pockets in isolation | Presence in pockets in complex (in the hexameric conformation) | Organism (of those used in the alignment of FIG. 5) that have, in their PilT, this residue in a corresponding position in alignments of primary structures |
|---|---|---|---|---|---|---|
| D160 | 5 | 30.00 | 16.00 | yes | — | all |
| D17 | 17 | 40.60 | 38.39 | yes | yes | all |
| D196 | 18 | 153.80 | 107.10 | — | yes | all |
| D198 | 16 | 40.00 | 36.25 | yes | yes | all |
| D207 | 2 | 20.00 | 15.00 | yes | yes | all |
| D242 | 4 | 41.20 | 17.95 | — | yes | all |
| D70 | 18 | 41.82 | 37.73 | yes | yes | all |
| E159 | 5 | 10.00 | 10.00 | yes | yes | all |
| E163 | 2 | 20.00 | 15.00 | yes | — | all |
| E204 | 1 | 20.00 | 20.00 | Yes | — | all |
| E209 | 2 | 40.00 | 25.00 | — | — | all |
| E219 | 17 | 45.30 | 29.52 | Yes | yes | all |
| H154 | 5 | 51.50 | 44.10 | — | — | all |
| H19 | 8 | 62.70 | 55.59 | — | — | all |
| H222 | 1 | 11.50 | 11.50 | — | — | all |
| H229 | 2 | 15.00 | 13.25 | yes | — | all |
| R176 | 2 | 42.10 | 41.80 | — | — | all |
| R194 | 18 | 101.80 | 79.91 | — | yes | all |
| R206 | 6 | 40.00 | 18.33 | yes | — | all |
| R239 | 16 | 60.00 | 34.87 | yes | yes | all |
| R29 | 18 | 104.10 | 86.07 | yes | yes | all |
| R294 | 7 | 40.00 | 14.46 | — | yes | all |
| R80 | 12 | 40.00 | 25.00 | yes | yes | all |
| R82 | 9 | 40.60 | 29.26 | yes | yes | all |
| R97 | 9 | 50.46 | 19.31 | yes | yes | all |
| E258 | 18 | 70.00 | 29.85 | yes | yes | All as Pt |

-continued

| Identification of the residue (amino acid and position) | Number of chains of XfPilT complexes in which the residue appears as a target | Maximum value of interface contact energy for the residue | Average value of interface contact energy for the residue | Presence in pockets in isolation | Presence in pockets in complex (in the hexameric conformation) | Organism (of those used in the alignment of FIG. 5) that have, in their PilT, this residue in a corresponding position in alignments of primary structures |
|---|---|---|---|---|---|---|
| E74 | 2 | 30.00 | 25.00 | — | yes | All as Pt |
| K235 | 13 | 40.60 | 22.54 | yes | yes | All as Pt |
| K249 | 2 | 10.00 | 10.00 | — | yes | All as Pt |
| R35 | 7 | 42.70 | 28.04 | — | yes | All as Pt |
| R90 | 6 | 46.40 | 19.53 | yes | yes | All as Pt |
| D33 | 16 | 41.20 | 28.21 | yes | yes | All as Pt |
| E248 | 2 | 20.00 | 15.00 | yes | — | All as Pt |
| R36 | 5 | 53.10 | 28.26 | — | — | All as Pt |
| D184 | 2 | 40.00 | 35.00 | — | yes | |
| E89 | 16 | 145.80 | 92.38 | — | yes | |
| K187 | 10 | 30.00 | 21.00 | — | — | |
| H152 | 17 | 84.10 | 47.41 | yes | yes | Xf, Ps, Dn |
| E336 | 5 | 40.00 | 28.30 | yes | yes | Xf, Xa, Ps, Pa, Rs, Dn |
| K58 | 2 | 72.60 | 46.30 | — | yes | Xf, Xa, Ps, Pa, Rs, Ng, Nm |
| R212 | 2 | 33.20 | 23.20 | — | — | Xf, Xa, Ps, Pa, Rs, Dn |
| R335 | 15 | 51.20 | 34.28 | yes | yes | Xf, Xa, Ps, Pa, Vc, Dn |
| E65 | 9 | 36.10 | 20.49 | yes | yes | Xf, Xa, Rs, Vc |
| E177 | 4 | 60.00 | 42.12 | — | yes | Xf, Xa, Ps, Pa, Rs, Aa |
| K170 | 1 | 10.00 | 10.00 | yes | — | Xf, Xa, Ps, Pa, Ng+, Nm+, Aa++ |
| E68 | 11 | 40.00 | 22.73 | yes | yes | Xf, Xa, Ps, Pa, Rs, Vc, Dn, Aa |
| E64 | 3 | 20.00 | 15.27 | — | — | Xf, Xa, Ps, Pa, Rs, Vc, Dn, Ng Nm, Aa, Ns, Ss+ |
| R290 | 18 | 108.80 | 78.48 | yes | — | Xf, Xa, Ps, Pa, Rs, Vc, Dn, Ng Nm, Ns, Ss |
| R180 | 1 | 10.00 | 10.00 | yes | — | Xf, Xa, Ps, Pa, Vc. Ns, Ss |
| D181 | 3 | 10.00 | 10.00 | yes | — | Xf, Xa, Ps, Pa, Rs, Vc, Dn+, Ng, Nm, Aa |
| H179 | 10 | 36.80 | 24.00 | — | yes | Xf, Xa, Ps, Pa, Vc, Dn, Aa, Ns, Ss |
| D62 | 1 | 21.50 | 21.50 | — | — | Xf, Xa, Ps, Vc, Dn, Ng, Nm |
| H183 | 1 | 10.00 | 10.00 | — | — | Xf, Xa, Ps, Pa, Vc+, Ss+ |
| E120 | 1 | 10.00 | 10.00 | — | — | Xf, Xa+, Ps+, Pa+, Dn+, Ng, Nm, Ns+, Ss |

Figure 4:
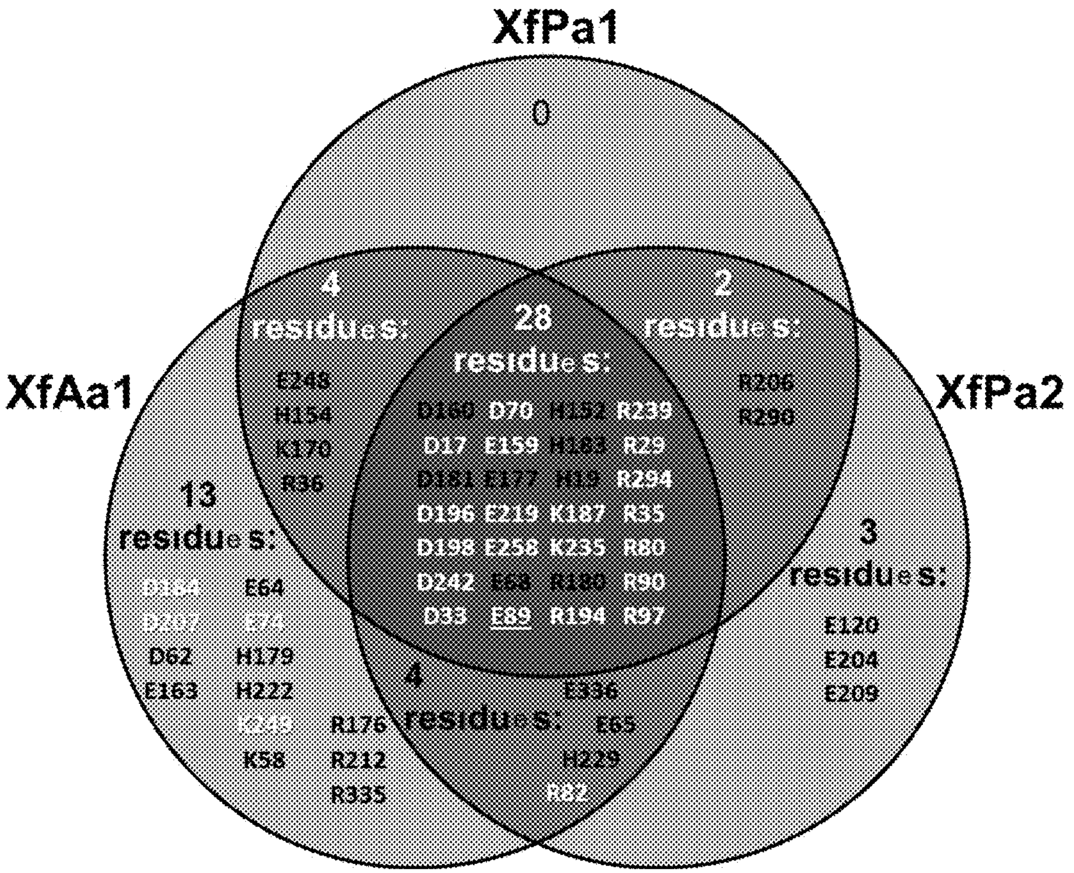
FIG. 4: a Venn diagram demonstrating the occurrence of the residues suggested as target (see table 2) in the three different complexes. (In this case, the occurrence is considered if the residue is present in at least one chain of the hexameric models of XfPilTs, with at least 10 kcal/mol of interface contact energy, more than 1 $Å^2$ of area exposed to the solvent when in complex, which have the characteristic of being capable of establishing hydrogen bridges and/or contacts of electrostatic nature and, preferably, that are located in pockets in complex and/or in isolation. The residues highlighted in white are located in pockets in complex (that is, in the hexameric conformation there is some adjacent pocket) on at least one chain. The residue E89 is underlined, because it will be used subsequently as an example of structural representation of a target.

Another important characteristic that will be considered upon designing drugs is the frequency of occurrence of the residue to be considered as a target in all the 18 possible chains in three modeled complexes. A determined residue may occur with these characteristics in only one conformation of the Xf PilT (as for example, residue E74 in the XfAa1 model), as can occur with these characteristics in all the three conformations (as for example, residue E89, which has such characteristics in the three hexamers: XfAa1, XfPa1 and XfPa2). The importance of this description lies in that fact that a determined drug may have, as a target, the binding on a residue at a given moment of the PilT protein (e.g.: if, in its bound state ATP, it exhibits structure of the hexamer, as we predicted in the XfPa2 model), on in various ones. The future processes of docking chemical compounds will have, as a target, one or more chains of one or more hexamers, according to the predicted characteristics of each target in each chain of each hexamer. Therefore, a Venn diagram was generated which contains the distribution of the 54 residues selected in the three hexamers modeled, as shown in FIG. 4.

With regard to the definition of the therapeutic targets, as already cited before, the anti-microbial drug design should be based on targets that are found mainly in the pathogens (not in non-pathogenic organism). In order to check whether, among the 54 residues selected, existed any residues of occurrence restricted to pathogenic organism such as Xf, Pa and other described before, with regard to non-pathogenic organisms (such as Aa) and even to organisms essential to the balance of ecosystems such as cyanobacteria (bacteria that photosynthesize and fixe atmospheric nitrogen), an alignment of primary structure was carried out, which included PilT of various organisms that include these categories and that are known in the literature on presence of the PilT, Type-IV Pilus and motility of the twitching type. This alignment, represented in FIG. 5, indicates that there is a high preservation of the IFRs, described above as potential targets, in this alignment of PilT sequences. This is one more possible evidence of the importance of the IFRs for pathogenic organisms that make use of the PilT IV. One may speculate that the sequences of the Proteobacterium PilT, being extremely preserved (Wall, D. and Kaiser, D. Type IV pili and cell motility. Mol Microbiol. 1999 April; 32(1):1-10. Review), would have their structure equally similar and, if so, the similarities and the differences observed in this alignment could also reflect the real characteristics of the structure.

In this alignment (FIG. 5), the 54 residues were contacted, and 25 of them occurred in all the organisms, coinciding with the position of the residue in XfPilT (D160, D17, D196, D198, D207, D242, D70, E159, E163, E204, E209, E219, H154, H19, H222, H229, R176, R194, R206, R239, R29, R294, R80, R82 and R97), which would constitute unspecific targets of the pathogens; 9 occurred in all the pathogenic Proteobacteria (E258, E74, K235, K249, R35, R90, D33, E248 and R36) constituting good targets for the development of drugs that reach this range of pathogens; 3 residues are exclusive of the *Xylella fastidiosa* PilT (D184, E89 and K187) which may constitute therapeutic targets for the development of drugs more specific to Xf PilT; 6 other residues occur in varied distribution, but still only in Xf and other pathogenic proteobacteria, but not in all of them (H152, E336, K58, R212, R335 and E65); and, finally, 17 residues that occur in varied distribution among Xf, other proteobacteria and always including Aa or some of the cyanobacteria, also constituting more unspecific targets (H152, E336, K58, R212, R335, E65, E177, K170, E68, E64, R290, R180, D181, H179, D62, H183 and E120).

In addition to the inclination of the possible therapeutic targets to the design of drugs against XfPilT, this analysis enables us to select them as to their possible specificity, since one aims at targets that occur preferably in Xf and/or other pathogenic bacteria of medical/economic interest. Therefore, the 18 targets called "preferred" herein for occurring only in Xf or in pathogenic proteobacteria are: D184, E89, K187, E258, E74, K235, K249, R35, R90, D33, E248, R36, H152, E336, K58, R212, R335 and E65 (but this does not present the other 36 residues from being used, but rather the 18 cited residues Will be preferred for designing drugs). Another interesting fact is that various charged residues that have the characteristic of contributing much in energetic terms to the XfPilT interfaces, which may be interpreted as a possible explanation for the statistically differences between the ICED values and the occurrence of areas of polar and charged residues among the Pa and Xf PilT hexamers and the Aa PilT hexamer.

Various hypotheses may be formulated to explain how these observations reflect on the function of the protein, performance and stability, and these may be discussed in future studies.

Thus, the most important amino acids among the IFRs, that is: the IFRs that establish more energetic contact are preserved within a group of pathogenic proteobacteria that make use of the PilT-dependent twitching motility as a moving mechanism. These preserved amino acids (summed to the specific ones for Xf) are those indicated as the preferred therapeutic targets for the development of drugs by physicochemical-structural complementarity, without invalidating the possibility of using the other residues (for instance, those which occur in all the organisms).

The main objective will be the production of a drug that binds in the future interface region of a certain monomer and prevents its oligomerization and/or prevents this drug from binding to oligomerized hexamer, in some of its conformations, and prevents the correct functioning of the interface and ATPasic activity.

Practical Example of Structure-Based Drug Design (SBDS)

Techniques of designing drugs on the basis of protein structure can be applied on the basis of possible therapeutic targets predicted. Hereinafter, one gives an exemplification of one of the various ways that can be adopted for the de novo design of drugs, which begins in mapping favorable interaction positions for functional groups (e.g.: in which positions one can design hydroxyl, amine, hydrophobic, cyclic groups, among others), or even small fragments of molecules. New compounds can then be developed de novo, so that relevant functional groups are located at positions that will determine a correct special relationship with the target site. After the design, one should proceed with modeling of its three-dimensional structure, docking tests, choice of the best ligands, prediction of the molecular/structural bases of their binding (e.g.: type of interactions that the latter is capable of carrying out). There is a number of software suitable for the de novo drug design and screening approaches, like the SPROUT (http:www.simbiosys.ca/sprout/), much used for the de novo design based on fragments. This program includes modules for identifying and selecting functional groups and positions on the target-sites to form initial fragments of compounds for generating structure (module EIeFAnT) and, as these are selected, skeletons are generated which meet the steric restrictions of the target-pocket by growing spacing fragments connecting them to the initial fragments (module SPIDEeR). Finally, one substitutes atoms on the skeleton until molecules are generated which are compatible with the electrostatic properties of the target-site (module MARABOU). The solutions may be characterized and have binding scores calculated by using the ALLigaTOR module.

Besides the de novo design of compounds, one aims at compounds that bind to the target-sites predicted by virtual screening on a large scale, by using databanks of three-dimensional structures of small molecules, as for example PubChem Compound (ftp://p.ncbi.nlm.nih/gov/pubchem/Compound_3D/), as a source of ligands to be used in screening against a target-site. The simulation of the protein-ligand interaction with a view to evaluating the capability of a ligand to form strong interactions and to fit into a target site is called "docking". Docking algorithms that include the following (but not limited thereto): Dock (Kuntz, I., Blaney, J., Oatley, S., Langridge, R., and Ferrin, T. 1982. A geometric approach to macromolecular-ligand interactions. J. Mol. Biol. 161, 269-288), FlexX (Kramer, B., Metz, G., Rarey, M., and Langauer, T. 1999. Ligand docking and screening with FlexX. Med. Chem. Res. 9, 463-478) AUTODOCK (Goodsell, D., Morris, G., and Olson, A. 1996. Automated docking of flexible ligands: applications of AutoDock. J. Mol. Recognit. 9, 1-5). MOL-DOCK (Thomsen, R., Christensen, M. H. MolDock: a new technique for high-accuracy molecular docking. J Med Chem. 2006 Jun. 1; 49(11):3315-21.) and GOLD (Jones, G., Willett, P., Glen, R. C., Leach, A. R., Taylor, R. Development and Validation of a Genetic Algorithm for Flexible Docking. J. Mol. Biol. 1997, 267, 727-748) can be used to carry out the "docking" in the region of interest to find the molecules that establish more favorable interactions that adapt better to the target site, being chosen by ranking the docking score.

In the example described hereinafter, one aims at the practical demonstration of one of the possible "pipeline" of how one could make the prediction of structure of compounds that will possibly bind to the targets predicted through a de novo design. The methodology is not limited to the molecules to be described in this context, but rather to all the molecules that Will be designed on the basis of the physicochemical and structural characteristics of the sites chosen as therapeutic sites, be it by means of a de novo design of drugs using fragments, software and prediction, virtual screening, screening using drugs or by other methods.

Figure 6:
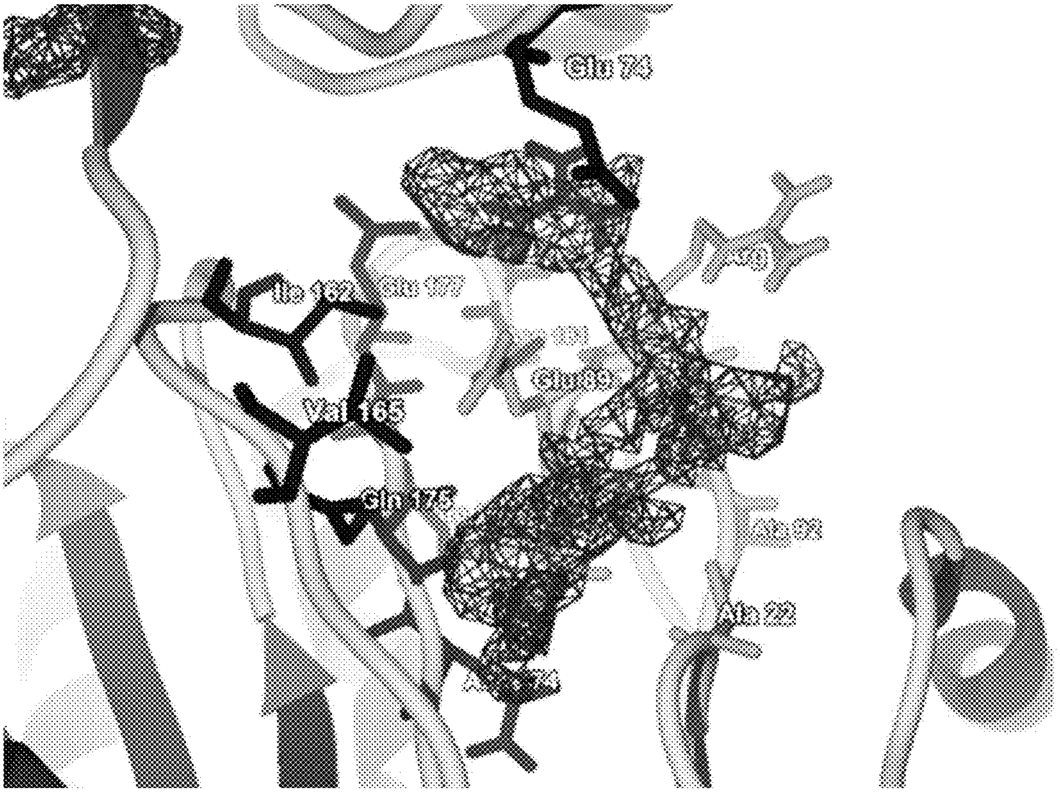
FIG. 6: structural representation of an example of a therapeutic target, the residue E89 on chain A of the XfAa1 complex, showing the adjacent residues that form the nanoenvironment in which the drug to be designed will bind. This target has been chosen to represent visually, since it is of extreme importance because it exists solely in the Xf_PilT and exists in all the three models (XfAa1, XfPa1 and XfPa2) containing "adjacent pocket", this being a very important characteristic to drug design.

About 50 compounds were designed de novo, based on the site which houses the target residue E89 of the chain A of the *Xylella fastidiosa* XfAa1 model using this residue considered to be exclusive of Xf, which suggests that the drug that will be designed on the basis of this target will possible be specified to the Xf PilT. First, the physicochemical and structural description of the target-site in question will be required, which can be seen in FIG. 6. In this structure, the E89 is located between the interfaces CTD$^{n}$: NTD$^{n+1}$, located in the NTD of the chain A and interacts with various residues in interface (Hydrogen bridge with Q175, two electrostatic interactions of reproduction with E74 and one hydrophobic interaction with I162, all of them of the chain F), resulting in a total of 23.8 Kcal/mol of interaction energy. By using the programs STING $^{J}$PD and Molegro Virtual Docker (MVD), one can observe that this residue is part of the adjacent pockets. The program MVD carried out the prediction of two pockets that surround the residue E89 (pocket 1 having 55.29 Å$^3$ of volume and pocket 2 with 45.05 Å$^3$ of volume). The fusion of these pockets gave rise to a new pocket of volume equal to 100.35 Å$^3$ and surface area equivalent to 381.44 Å$^3$, as shown in FIG. 6. The residues adjacent this pocket (at a distance of less than 6 Å) include, in addition to the E89, two more negatively charged residues (Glu 177 and Glu 74 of the chain F), three positively charged residues (Arg90 and Lys45 of the chain A and Arg180 and Arg80), eight apolar residues (Ile162, Val165, Leu172 an Ile173 of the chain F, Ala22, Gly23, Leu24 and Ala92 of the chain A) and three polar residues (Gln88 and Asn87 of the chain A and Gln 175 of the chain F).

Thus, following the structure of the pocket with regard to the limits thereof and atom sizes, one designed about 40 chemical structures of drugs that would possibly Interact with the mentioned region, mainly with the target-sites predicted and located close to the pocket E89 (residue exclusive of Xf), R90 and E74 (residues exclusive of pathogenic proteobacteria). The paper began with the design of four base-structures using the program ChemDraw (http://www.cambridgesoft.com/) and modeling the three-dimensional structure in the module Chem3Dpro. This module further enabled the small molecules modeled in 3D to undergo minimization of energy and molecular dynamics to achieve an acceptable structural conformation. These designed structures have certain characteristics in common: presence of two cyclic ends, which may be: 5-carbon ring and 6-carbon ring (either aromatic or not), for interaction with apolar residues and occupation of the wide spaces of the pocket, a spacing carbonic region between the rings (between four and five carbons), a group of ionizable carboxyl group bound to one of the rings for interaction (preferably of electrostatic order) with the Arg90, closest to the pocket, one or more ionizable amine groups for interaction with the polar and negative residues and presence or absence of hydroxyl groups.

Then a docking simulation was carried out (with the flexible ligand) by using the program MVD, centered on the mentioned pocket and with a search space radius of 15 Å. The algorithm for score calculation used was the MolDock Score [GRID], using a Grid resolution of 0.3 Å (evaluating the ligand by means of internal interactions of hydrogen bridges, electrostatic interactions and distortions $Sp^2$-$Sp^2$). The search and docketing algorithm used was the MolDock Optimizer (which is na implementation of a variation of the evolutionary algorithm), with 10 runs, population size equal to 100 and with 3000 interactions. After docketing, the MVD carried out minimization of energy and optimization of hydrogen bridge.

Figure 7:
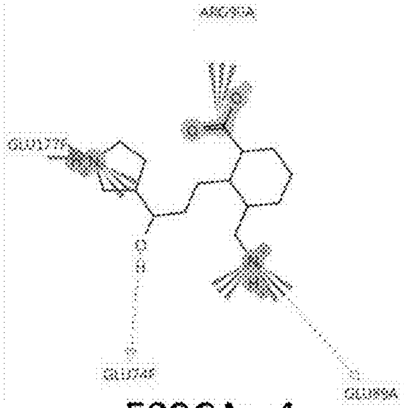
FIG. 7: a 2-D representation (obtained by mounting images taken from the software Ligand Scout) of the designed and modeled drugs that obtained the best MolDock Score vectors in each of the docking runs carried out. One carried out five docking runs, the first one being carried out with compounds designed directly from the characteristics of the target site. The next runs were carried out with molecules that were designed on the basis of the best compounds of the preceding runs, the E89C4m4 being obtained in the second run, E89C4m30 in the third one, E89C4m32 in the fourth one and E89C4m34 in the fifth run and classified as being the best candidate to bind to the target-site E89. With dotted arrows one represent hydrogen bridges that the compound establishes with residues from the target-site; three gray triangles represent the ionizable atoms and adjacent to this representation are the identifications of residue from the target-sites that interact electrostatically with the atom in question; the occurrence of hydrophobic interactions is represented with two curved lines in clear gray. There are more details in the portion of the figure that has the 2-D image of the E89C4m34 compound that may be suggested (among the compounds designed) as the one that is most likely to bind to the target site. One represents a distance (12.22 Å) of the atom 18 to 8, which shows the correspondence with the size of the cavity (which is about 14 Å long in its lowest portion, the atoms are numbered (following the numbering of the Chem Draw) and are present in the isomeric forms of the compound.
Figure 7:
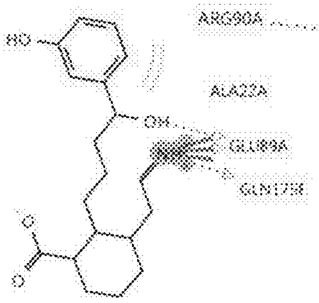
Figure 7:
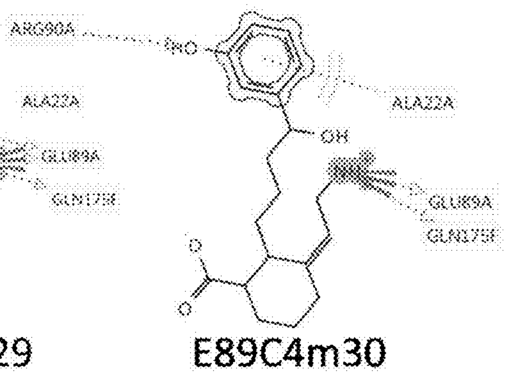
Figure 7:
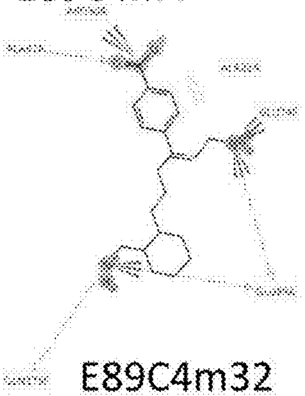
Figure 7:
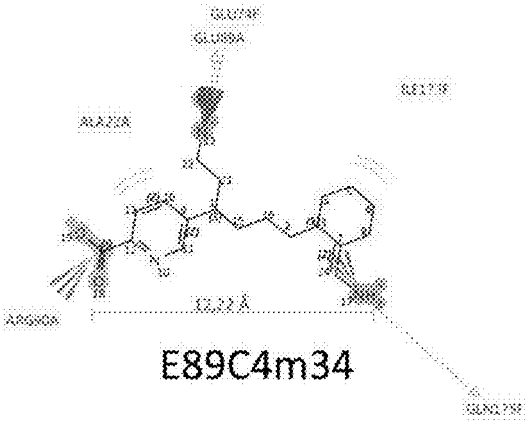

Of the four designed and modeled base-structures, the compounds that achieved the Best dock score thereof (−1105.62) was called E89C4m4. Subsequently, evaluating that the atoms could be altered/withdrawn/added to optimize the binding to the target-site and, specifically, to the target site (E89), changes were made through the ChemDraw and a new modeling was made by using Chem3Dpro. In this way, one carried out, in all, four additional docking runs with molecules that were designed on the basis of the Best compounds of the preceding runs. The compounds with the best MolDock Scores of each of the Five runs (E89Cm4, E89Cm29, E89C4m30, E89C4m32 and E89C4m34), like the portions developed in the interactions and the residues that would with the molecule in question are represented in FIG. 7 and the data referring to the docking of these ligands are shown in Table 3. At the end, one obtained a structure with better MolDock Score value (−131.118), which establishes−142.72 Kcal/mol of interaction energy with the protein.

TABLE 3

Data referring to the "docking" of the molecules cited and the MolDock Score values obtained, protein interaction energy, energies referring to electrostatic interactions of short distance, (lower than 4.5 Å) and (higher than 4.5 Å), energy associated to the establishment of long distance hydrogen bridges (wherein all the energy values are given in Kcal/mol), number of heavy atoms and molecular weight of each compound and the ligand reference (LE1) given as the ratio between the MolDock Score and the number of heavy atoms.

| Ligand | MolDock Score | Interaction | Electrostatic interaction (short distance) | Electrostatic interaction (long distance) | Hydrogen bridges | Heavy Atoms | Molecular weight | Ligad efficiency |
|---|---|---|---|---|---|---|---|---|
| E89C4 M34 | −131.118 | −142.772 | −22.8288 | −2.55371 | −6.36607 | 24 | 333.468 | −5.46237 |
| E89C4 M30 | −124.067 | −128.484 | 0 | 0 | −11.3605 | 24 | 333.422 | −5.16945 |
| E89C4 M29 | −120.767 | −127.069 | 0 | 0 | −6.8006 | 24 | 333.4222 | −5.03195 |
| E89C4 M32 | −111.706 | −133.849 | −21.9648 | −1.95334 | −7.15845 | 24 | 332.48 | −4.6544 |
| E89C4 M4 | −105.62 | −108.811 | −17.8373 | −0.42324 | −5.55281 | 20 | 283.386 | −5.281 |

The compounds herein called E89C4m34 (FIG. 7) has the formula $C_{19}H_{32}N_3O_2$, notation SMILES [O—]C(═O)C2=CC═C(C(CCCC\1CCCCC1=C/[NH3+])CC[NH3+])CN2, molecular weight of 334.484 Da, 56 atoms (24 of which are heavy), 11 rotary ligand, 2 rings, one of which is aromatic. One used the program Ligand Scout for prediction of some polar and chemical characteristics such as the octhanol/water partition coefficient (Log P), which influences the properties ADME (Absorption, Distribution, Metabolization and Excretion) of the drug by indicting the lipophilicity of the compound. The E89C4m34 has c Log P of −0.923, which indicates that it is water-soluble, and with TPSA (Total Polar Surface Area) of 108 Å$^2$. It further has 3 hydrogen-bridge donating atoms (atom N 23 which establishes hydrogen bridges with the residues Glu89A and Glu74F, atom N 17 which establishes hydrogen bridge with Gln175F, and atom N 10), hydrogen bridge accepting atoms (O19 e O20), a negatively ionizable one (O19, which interacts strongly through short-distance attractive electrostatic interactions (less than 4.5 Å) with Arg90A) and two positively ionizable ones (atoms N 17 and N 23, the latter being responsible for two strong short-distance attractive electrostatic interactions with the residues E89A and E74F). The rings are important to the development of hydrophobic interactions with apolar residues of the target-site such as Ala22A and Ile173F, Table 04.

TABLE 4

Data referring to the targets of interaction of the compound E89C4m34 with the target-side, showing which chain it belongs to, its name, identification, total energy established in contacts and energy from short- and long-distance electrostatic interaction.

| Target chain | Amino acido | Identification of the residue | Total energy established with the residue | Energy from long-distance electrostatic (r > 4.5) | Energy from short-distance electrostatic interaction (r > 4.5) |
|---|---|---|---|---|---|
| XfAa1[A] | Glu | 89 | −41.3234 | −1.02331 | −14.3845 |
| XfAa1[A] | Arg | 90 | −18.0581 | 0.457393 | −1.18196 |
| XfAa1[F] | Glu | 74 | −13.1333 | −0.00599243 | −7.26196 |
| XfAa1[F] | Gln | 175 | −9.68925 | | |
| XfAa1[A] | Lys | 45 | −8.52262 | −1.34031 | |
| XfAa1[A] | Gly | 23 | −7.64588 | | |
| XfAa1[A] | Ala | 22 | −7.18962 | | |
| XfAa1[F] | Ile | 173 | −7.06743 | | |
| XfAa1[A] | Gln | 88 | −5.28542 | | |
| XfAa1[A] | Gly | 91 | −5.21324 | | |
| XfAa1[F] | His | 166 | −3.54791 | 0.877045 | |
| XfAa1[F] | Thr | 167 | −3.28522 | | |
| XfAa1[F] | Val | 165 | −2.68033 | | |
| XfAa1[F] | Asn | 174 | −2.24359 | | |
| XfAa1[F] | Ser | 168 | −1.96354 | | |
| XfAa1[F] | Glu | 159 | −1.70918 | −1.70918 | |
| XfAa1[F] | Glu | 177 | −1.44564 | −1.44564 | |
| XfAa1[F] | Asp | 181 | −1.38837 | −1.38837 | |
| XfAa1[A] | Leu | 24 | −1.37025 | | |
| XfAa1[A] | Ser | 21 | −1.25635 | | |
| XfAa1[A] | Ala | 92 | −0.65466 | | |
| XfAa1[A] | Val | 47 | −0.45698 | | |
| XfAa1[F] | Asp | 145 | −0.38244 | −0.382442 | |
| XfAa1[F] | Glu | 163 | −0.34223 | −0.342231 | |
| XfAa1[A] | His | 44 | −0.30635 | | |
| XfAa1[F] | Lys | 149 | 0.308608 | 0.308608 | |
| XfAa1[F] | Lys | 102 | 0.442583 | 0.442583 | |
| XfAa1[F] | Arg | 180 | 1.21.20099 | 1.20099 | |
| XfAa1[F] | Arg | 80 | 1.73437 | 2.22489 | |

Figure 8:
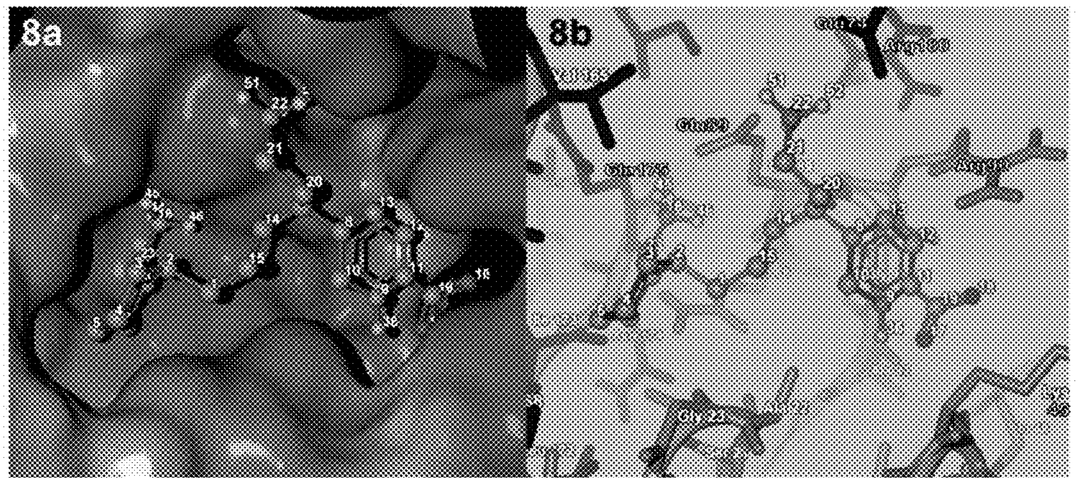
FIG. 8: Representation of the surfaces that delimit the "pocket" and that compose the target site of binding is shown (8*a*), showing how the ligand has a shape similar to that of the region. In 8*b* one represents the E89C4m34 and the 3-D positions of the residues that interact with this molecule in the "stick" format.

The complete listing of the residues that Interact with the compounds, as well as the total energy established between them and the atoms of the E89C4m34 and the energy established through short-distance and long-distance electrostatic interaction. The residues that establish the strongest interactions are: E89 and R90 of the chain A (−41.32 and −18.05 Kcal/mol, respectively) and with E74 of the chain F (−13.13 Kcal/mol), which are residues included in the list of therapeutic targets exclusive of pathogenic proteobacteria, wherein E89 exclusive of Xf. The representation of the surfaces that delimit the pocket, which compose the binding target site is shown in figure EP, showing how the ligand has a shape similar to that of the region. In FIG. 8*b* one represented the E89C4m34 and the positions of the residues that interact with this molecule.

In this patent application we have demonstrated the methodology for identifying specific therapeutic targets for the design of new drugs in modeled structures of the *Xylella fastidiosa* Pilt and that has possible application for pathogenic organism which also have this protein with a high degree of sequence similarity and correspondence in the residues indicated as targets in alignment of primary structure. Then we provide a list of 54 target residues to be used in process of structure-based design, 18 of which will be preferably used. Finally, we proposed computational-design Technologies were proposed, as well as a few structures of chemical compounds for Binding on the target site E89 of the Xf PilT. The characterization of the interaction between the designed compound, which has the highest energies of interaction with the corresponding target in the Xf PilT (herein this compound is called E89C4m34) was described in detail, embracing physicochemical and structural characteristics. It is important to point out that the present patent application is not limited to the drugs cited, but rather its methodology for identifying target-residues in the protein PilT, the target residues suggested for the drug design and the proposal of methods can culminate in the design/identification of various liable to be used for preventing the correct functioning of the PilT (be it by preventing oligomerization or by preventing the dynamics of the interface in the hexamer formed). The drug suggested is only one of the examples of the work that is being carried out.

The invention claimed is:

1. A method for identifying drug candidates that inhibit motility of PilT-expressing *Xylella fastidiosa*, comprising:

(a) selecting at least one interface-forming residue from a PilT protein from a PilT-expressing *Xylella fastidiosa* as a therapeutic target site, wherein said at least one interface-forming residue is selected from the group consisting of residue D184, E89, K187, E258, E74, K235, K249, R35, R90, D33, E248, R36, H152, E336, K58, R212, R335 and E65 from *Xylella fastidiosa* PilT; and (b) identifying at least one drug candidate predicted to bind to said therapeutic target site, wherein said identifying comprises one or more of de novo drug design and virtual screening.

* * * * *

SEQUENCE LISTING

<160> NUMBER OF SEQ ID NOS: 12

<210> SEQ ID NO 1
<211> LENGTH: 344
<212> TYPE: PRT
<213> ORGANISM: Xylella fastidiosa

<400> SEQUENCE: 1

```
Met Asp Ile Ala Glu Leu Leu Ala Phe Ser Val Lys Asn Asn Ala Ser
1               5                   10                  15

Asp Leu His Leu Ser Ala Gly Leu Pro Pro Met Ile Arg Val Asp Gly
            20                  25                  30

Asp Val Arg Arg Ile Asn Ile Pro Ala Phe Asp His Lys Gln Val Gln
        35                  40                  45

Ser Leu Ile Tyr Asp Ile Met Ser Asp Lys Gln Arg Arg Asp Tyr Glu
    50                  55                  60

Glu Ala Leu Glu Thr Asp Phe Ser Phe Glu Ile Pro Ser Leu Ser Arg
65                  70                  75                  80

Phe Arg Val Asn Ala Phe Asn Gln Glu Arg Gly Ala Gly Ala Val Phe
                85                  90                  95

Arg Thr Ile Pro Asn Lys Val Met Thr Leu Asp Glu Leu Gly Cys Leu
            100                 105                 110

Pro Val Phe Arg Lys Leu Ile Glu Glu Pro Gln Gly Leu Ile Leu Val
        115                 120                 125

Thr Gly Pro Thr Gly Ser Gly Lys Ser Thr Thr Leu Ala Ala Met Ile
    130                 135                 140

Asp His Ile Asn Lys Asn Ala His Gly His Ile Leu Thr Ile Glu Asp
145                 150                 155                 160

Pro Ile Glu Phe Val His Thr Ser Gln Lys Cys Leu Ile Asn Gln Arg
                165                 170                 175

Glu Val His Arg Asp Thr His Asp Phe Asn Lys Ala Leu Ser Ser Ala
            180                 185                 190

Leu Arg Glu Asp Pro Asp Ile Ile Leu Ile Gly Glu Leu Arg Asp Leu
        195                 200                 205

Glu Thr Ile Arg Leu Ala Leu Thr Ala Ala Glu Thr Gly His Leu Val
    210                 215                 220

Phe Gly Thr Leu His Thr Asn Ser Ala Ala Lys Ser Ile Asn Arg Ile
225                 230                 235                 240

Ile Asp Val Phe Pro Ala Ala Glu Lys Pro Met Val Arg Ser Met Leu
                245                 250                 255

Ser Glu Ser Leu Cys Gly Ile Ile Ser Gln Met Leu Leu Lys Lys Val
            260                 265                 270

Gly Gly Gly Arg Thr Ala Ala Trp Glu Ile Met Val Gly Thr Pro Ala
        275                 280                 285

Ile Arg Asn Leu Ile Arg Glu Asp Lys Val Ala Gln Met Tyr Ser Ser
    290                 295                 300

Ile Gln Thr Gly Gln Gln Tyr Gly Met Gln Thr Leu Asp Gln His Leu
305                 310                 315                 320

Gln Asp Leu Ile Lys Arg Asn Leu Ile Thr Arg Gln Gln Ala Arg Glu
                325                 330                 335

Tyr Ala Lys Asp Lys Ala Asn Phe
            340
```

<210> SEQ ID NO 2
<211> LENGTH: 345

<212> TYPE: PRT
<213> ORGANISM: Xanthomonas axonoodis

<400> SEQUENCE: 2

Met Asp Ile Ala Glu Leu Leu Ala Phe Ser Val Lys Asn Lys Ala Ser
1 5 10 15

Asp Leu His Leu Ser Ala Gly Leu Pro Pro Met Ile Arg Val Asp Gly
20 25 30

Asp Val Arg Arg Ile Asn Ile Pro Ala Leu Asp His Lys Gln Val His
35 40 45

Ala Leu Val Tyr Asp Ile Met Ser Asp Lys Gln Arg Arg Asp Tyr Glu
50 55 60

Glu Phe Leu Glu Val Asp Phe Ser Phe Glu Ile Pro Ser Leu Ala Arg
65 70 75 80

Phe Arg Val Asn Ala Phe Asn Gln Asn Arg Gly Ala Gly Ala Val Phe
85 90 95

Arg Thr Ile Pro Ser Glu Val Leu Thr Leu Glu Asp Leu Gly Cys Pro
100 105 110

Pro Ile Phe Arg Gln Leu Ile Asp Gln Pro Gln Gly Leu Ile Leu Val
115 120 125

Thr Gly Pro Thr Gly Ser Gly Lys Ser Thr Thr Leu Ala Gly Met Ile
130 135 140

Asp Tyr Ile Asn Lys Asn Glu Tyr Gly His Ile Leu Thr Val Glu Asp
145 150 155 160

Pro Ile Glu Phe Val His Thr Ser Gln Lys Cys Leu Ile Asn Gln Arg
165 170 175

Glu Val His Arg Asp Thr His Gly Phe Asn Glu Ala Leu Arg Ser Ala
180 185 190

Leu Arg Glu Asp Pro Asp Ile Ile Leu Val Gly Glu Leu Arg Asp Leu
195 200 205

Glu Thr Ile Arg Leu Ala Leu Thr Ala Ala Glu Thr Gly His Leu Val
210 215 220

Phe Gly Thr Leu His Thr Ser Ser Ala Ala Lys Thr Ile Asp Arg Ile
225 230 235 240

Ile Asp Val Phe Pro Ala Gly Glu Lys Pro Met Val Arg Ser Met Leu
245 250 255

Ser Glu Ser Leu Arg Ala Val Ile Ser Gln Ala Leu Leu Lys Lys Val
260 265 270

Gly Gly Gly Arg Thr Ala Ala Trp Glu Ile Met Val Gly Thr Pro Ala
275 280 285

Ile Arg Asn Leu Ile Arg Glu Asp Lys Val Ala Gln Met Tyr Ser Ser
290 295 300

Ile Gln Thr Gly Gln Gln Tyr Gly Met Gln Thr Leu Asp Gln His Leu
305 310 315 320

Gln Asp Leu Val Lys Arg Ser Leu Ile Thr Arg Asn Gln Ala Arg Glu
325 330 335

Tyr Ala Lys Asp Lys Arg Ile Phe Glu
340 345

<210> SEQ ID NO 3
<211> LENGTH: 344
<212> TYPE: PRT
<213> ORGANISM: Pseudomonas syringae

<400> SEQUENCE: 3

-continued

```
Met Asp Ile Thr Glu Leu Leu Ala Phe Ser Ala Lys Gln Gly Ala Ser
1               5                   10                  15

Asp Leu His Leu Ser Ala Gly Leu Pro Pro Met Ile Arg Val Asp Gly
            20                  25                  30

Asp Val Arg Arg Ile Asn Leu Pro Pro Leu Asp Ala Lys Glu Val Lys
        35                  40                  45

Ala Leu Ile Tyr Asp Ile Met Asn Asp Lys Gln Arg Gln Asp Phe Glu
    50                  55                  60

Glu Arg Leu Glu Thr Asp Phe Ser Phe Glu Val Pro Gly Val Ala Arg
65                  70                  75                  80

Phe Arg Val Asn Ala Phe Asn Gln Asn Arg Gly Ala Gly Ala Val Phe
                85                  90                  95

Arg Thr Ile Pro Ser Lys Ile Leu Ser Met Glu Asp Leu Gly Met Gly
            100                 105                 110

Ser Val Phe Arg Lys Ile Thr Asp Val Ala Arg Gly Leu Ile Leu Val
        115                 120                 125

Thr Gly Pro Thr Gly Ser Gly Lys Ser Thr Thr Leu Ala Ala Met Ile
    130                 135                 140

Asp Tyr Leu Asn Cys Asn Lys His His His Ile Leu Thr Ile Glu Asp
145                 150                 155                 160

Pro Ile Glu Phe Val His Glu Ser Lys Lys Cys Leu Val Asn Gln Arg
                165                 170                 175

Glu Val His Arg Asp Thr Leu Gly Phe Ser Glu Ala Leu Arg Ser Ala
            180                 185                 190

Leu Arg Glu Asp Pro Asp Val Ile Leu Val Gly Glu Met Arg Asp Leu
        195                 200                 205

Glu Thr Ile Arg Leu Ala Leu Thr Ala Ala Glu Thr Gly His Leu Val
    210                 215                 220

Phe Gly Thr Leu His Thr Thr Ser Ala Ala Lys Thr Ile Asp Arg Ile
225                 230                 235                 240

Val Asp Val Phe Pro Ala Gln Glu Lys Ser Met Ile Arg Ser Met Leu
                245                 250                 255

Ser Glu Ser Leu His Ala Val Val Ser Gln Ala Leu Leu Lys Lys Val
            260                 265                 270

Gly Gly Gly Arg Val Ala Ala His Glu Ile Met Met Gly Thr Pro Ala
        275                 280                 285

Ile Arg Asn Leu Ile Arg Glu Asp Lys Val Ala Gln Met Tyr Ser Ser
    290                 295                 300

Ile Gln Thr Gly Gly Ser Leu Gly Met Gln Thr Leu Asp Met Cys Leu
305                 310                 315                 320

Ala Asp Leu Val Lys Lys Gly Leu Ile Thr Arg Glu Ser Ala Arg Glu
                325                 330                 335

Arg Ala Lys Val Pro Asp Asn Phe
            340
```

<210> SEQ ID NO 4
<211> LENGTH: 348
<212> TYPE: PRT
<213> ORGANISM: Pseudomonas aeruginosa

<400> SEQUENCE: 4

```
Met Asp Ile Thr Glu Leu Leu Ala Phe Ser Ala Lys Gln Gly Ala Ser
1               5                   10                  15

Asp Leu His Leu Ser Ala Gly Leu Pro Pro Met Ile Arg Val Asp Gly
            20                  25                  30
```

```
Asp Val Arg Arg Ile Asn Leu Pro Pro Leu Glu His Lys Gln Val His
        35                  40                  45

Ala Leu Ile Tyr Asp Ile Met Asn Asp Lys Gln Arg Lys Asp Phe Glu
    50                  55                  60

Glu Phe Leu Glu Thr Asp Phe Ser Phe Glu Val Pro Gly Val Ala Arg
65                  70                  75                  80

Phe Arg Val Asn Ala Phe Asn Gln Asn Arg Gly Ala Gly Ala Val Phe
                85                  90                  95

Arg Thr Ile Pro Ser Lys Val Leu Thr Met Glu Glu Leu Gly Met Gly
            100                 105                 110

Glu Val Phe Lys Arg Val Ser Asp Val Pro Arg Gly Leu Val Leu Val
        115                 120                 125

Thr Gly Pro Thr Gly Ser Gly Lys Ser Thr Thr Leu Ala Ala Met Leu
    130                 135                 140

Asp Tyr Leu Asn Asn Thr Lys Tyr His His Ile Leu Thr Ile Glu Asp
145                 150                 155                 160

Pro Ile Glu Phe Val His Glu Ser Lys Lys Cys Leu Val Asn Gln Arg
                165                 170                 175

Glu Val His Arg Asp Thr Leu Gly Phe Ser Glu Ala Leu Arg Ser Ala
            180                 185                 190

Leu Arg Glu Asp Pro Asp Ile Ile Leu Val Gly Glu Met Arg Asp Leu
        195                 200                 205

Glu Thr Ile Arg Leu Ala Leu Thr Ala Ala Glu Thr Gly His Leu Val
    210                 215                 220

Phe Gly Thr Leu His Thr Thr Ser Ala Ala Lys Thr Ile Asp Arg Val
225                 230                 235                 240

Val Asp Val Phe Pro Ala Glu Glu Lys Ala Met Val Arg Ser Met Leu
                245                 250                 255

Ser Glu Ser Leu Gln Ser Val Ile Ser Gln Thr Leu Ile Lys Lys Ile
            260                 265                 270

Gly Gly Gly Arg Val Ala Ala His Glu Ile Met Ile Gly Thr Pro Ala
        275                 280                 285

Ile Arg Asn Leu Ile Arg Glu Asp Lys Val Ala Gln Met Tyr Ser Ala
    290                 295                 300

Ile Gln Thr Gly Gly Ser Leu Gly Met Gln Thr Leu Asp Met Cys Leu
305                 310                 315                 320

Lys Gly Leu Val Ala Lys Gly Leu Ile Ser Arg Glu Asn Ala Arg Glu
                325                 330                 335

Lys Ala Lys Ile Pro Glu Asn Phe Gly Ala Ala Ala
            340                 345
```

<210> SEQ ID NO 5
<211> LENGTH: 348
<212> TYPE: PRT
<213> ORGANISM: Dichelobacter nodosus

<400> SEQUENCE: 5

```
Lys Lys Glu Leu Lys Leu Asp Asp Leu Leu Arg Phe Ala Gln Lys Gln
1               5                   10                  15

Gly Ala Ser Asp Leu His Leu Ser Cys Gly Val Pro Pro Met Ile Arg
            20                  25                  30

Ile Asp Gly Asp Val Arg Arg Leu Asn Leu Pro Pro Leu Gln Asn Gln
        35                  40                  45

Gln Met Arg Asp Met Ile Phe Gly Ile Met Thr Asp Ala Gln Met Lys
```

-continued 50 55 60

Ser Phe Glu Glu Lys Trp Glu Ala Asp Phe Ser Thr Glu Ile Arg Gly
65 70 75 80

Val Ser Arg Phe Arg Val Asn Val Phe Gln Gln Asn Arg Gly Met Gly
85 90 95

Ile Val Phe Arg Thr Ile Pro Ser Lys Val Leu Ser Leu Glu Asp Leu
100 105 110

Lys Ala Pro Ala Lys Phe Val Asp Ile Ile Asp Val Pro Arg Gly Leu
115 120 125

Val Leu Val Thr Gly Pro Thr Gly Ser Gly Lys Ser Thr Thr Leu Ala
130 135 140

Ala Met Ile Asp His Ile Asn Asn Asn Arg His Glu His Ile Leu Thr
145 150 155 160

Val Glu Asp Pro Ile Glu Phe Val His Glu Ser Lys Lys Cys Leu Val
165 170 175

Asn Gln Arg Glu Val His Arg Asp Thr Gln Ser Phe Ser Asn Ala Leu
180 185 190

Arg Ala Ala Leu Arg Glu Asp Pro Asp Ile Ile Leu Val Gly Glu Leu
195 200 205

Arg Asp Leu Glu Thr Ile Arg Leu Ala Leu Thr Ala Ala Glu Thr Gly
210 215 220

His Leu Val Phe Gly Thr Leu His Thr Ser Ser Ala Ala Lys Thr Ile
225 230 235 240

Asp Arg Ile Ile Asp Val Phe Pro Gly Glu Glu Lys Gln Leu Val Arg
245 250 255

Ser Met Leu Ser Glu Ser Leu Arg Ala Val Ile Ala Gln Thr Leu Leu
260 265 270

Lys Lys Ile Gly Gly Gly Arg Val Ala Ala His Glu Val Leu Val Gly
275 280 285

Thr Ser Ala Val Lys Asn Leu Ile Arg Glu Asp Lys Val Ala Gln Ile
290 295 300

Tyr Ser Thr Ile Gln Thr Gly Ser Gln Tyr Gly Met Gln Thr Leu Asp
305 310 315 320

Gln Ala Leu Ser Ala Leu Val Lys Glu Gly Lys Val Asp Arg Met Leu
325 330 335

Ala Ala Ser Lys Ala His Asp Lys Asp Asn Phe Met
340 345

<210> SEQ ID NO 6
<211> LENGTH: 347
<212> TYPE: PRT
<213> ORGANISM: Neisseria gonorrhoeae

<400> SEQUENCE: 6

Met Gln Ile Thr Asp Leu Leu Ala Phe Gly Ala Lys Asn Lys Ala Ser
1 5 10 15

Asp Leu His Leu Ser Ser Gly Ile Ser Pro Met Ile Arg Val His Gly
20 25 30

Asp Met Arg Arg Ile Asn Leu Pro Glu Met Ser Ala Glu Glu Val Gly
35 40 45

Asn Met Val Thr Ser Val Met Asn Asp His Gln Arg Lys Ile Tyr Gln
50 55 60

Gln Asn Leu Glu Val Asp Phe Ser Phe Glu Leu Pro Asn Val Ala Arg
65 70 75 80

-continued

```
Phe Arg Val Asn Ala Phe Asn Thr Gly Arg Gly Pro Ala Ala Val Phe
                85                  90                  95

Arg Thr Ile Pro Ser Thr Val Leu Ser Leu Glu Glu Leu Lys Ala Pro
            100                 105                 110

Ser Ile Phe Gln Lys Ile Ala Glu Ser Pro Arg Gly Met Val Leu Val
        115                 120                 125

Thr Gly Pro Thr Gly Ser Gly Lys Ser Thr Thr Leu Ala Ala Met Ile
    130                 135                 140

Asn Tyr Ile Asn Glu Thr Gln Pro Ala His Ile Leu Thr Ile Glu Asp
145                 150                 155                 160

Pro Ile Glu Phe Val His Gln Ser Lys Lys Ser Leu Ile Asn Gln Arg
                165                 170                 175

Glu Leu His Gln His Thr Leu Ser Phe Ala Asn Ala Leu Ser Ser Ala
            180                 185                 190

Leu Arg Glu Asp Pro Asp Val Ile Leu Val Gly Glu Met Arg Asp Pro
        195                 200                 205

Glu Thr Ile Gly Leu Ala Leu Thr Ala Ala Glu Thr Gly His Leu Val
    210                 215                 220

Phe Gly Thr Leu His Thr Thr Gly Ala Ala Lys Thr Val Asp Arg Ile
225                 230                 235                 240

Val Asp Val Phe Pro Ala Gly Glu Lys Glu Met Val Arg Ser Met Leu
                245                 250                 255

Ser Glu Ser Leu Thr Ala Val Ile Ser Gln Asn Leu Leu Lys Thr His
            260                 265                 270

Asp Gly Asn Gly Arg Val Ala Ser His Glu Ile Leu Ile Ala Asn Pro
        275                 280                 285

Ala Val Arg Asn Leu Ile Arg Glu Asn Lys Ile Thr Gln Ile Asn Ser
    290                 295                 300

Val Leu Gln Thr Gly Gln Ala Ser Gly Met Gln Thr Met Asp Gln Ser
305                 310                 315                 320

Leu Gln Ser Leu Val Arg Gln Gly Leu Ile Ala Pro Glu Ala Ala Arg
                325                 330                 335

Arg Arg Ala Gln Asn Ser Glu Ser Met Ser Phe
            340                 345


<210> SEQ ID NO 7
<211> LENGTH: 347
<212> TYPE: PRT
<213> ORGANISM: Neisseria meningitidis

<400> SEQUENCE: 7

Met Gln Ile Thr Asp Leu Leu Ala Phe Gly Ala Lys Asn Lys Ala Ser
1               5                   10                  15

Asp Leu His Leu Ser Ser Gly Ile Ser Pro Met Ile Arg Val His Gly
            20                  25                  30

Asp Met Arg Arg Ile Asn Leu Pro Glu Met Ser Ala Glu Glu Val Gly
        35                  40                  45

Asn Met Val Thr Ser Val Met Asn Asp His Gln Arg Lys Ile Tyr Gln
    50                  55                  60

Gln Asn Leu Glu Val Asp Phe Ser Phe Glu Leu Pro Asn Val Ala Arg
65                  70                  75                  80

Phe Arg Val Asn Ala Phe Asn Thr Gly Arg Gly Pro Ala Ala Val Phe
                85                  90                  95

Arg Thr Ile Pro Ser Thr Val Leu Ser Leu Glu Glu Leu Lys Ala Pro
            100                 105                 110
```

```
Ser Ile Phe Gln Lys Ile Ala Glu Ser Pro Arg Gly Met Val Leu Val
        115                 120                 125

Thr Gly Pro Thr Gly Ser Gly Lys Ser Thr Thr Leu Ala Ala Met Ile
    130                 135                 140

Asn Tyr Ile Asn Glu Thr Gln Pro Ala His Ile Leu Thr Ile Glu Asp
145                 150                 155                 160

Pro Ile Glu Phe Val His Gln Ser Lys Lys Ser Leu Ile Asn Gln Arg
                165                 170                 175

Glu Leu His Gln His Thr Leu Ser Phe Ala Asn Ala Leu Ser Ser Ala
            180                 185                 190

Leu Arg Glu Asp Pro Asp Val Ile Leu Val Gly Glu Met Arg Asp Pro
        195                 200                 205

Glu Thr Ile Gly Leu Ala Leu Thr Ala Ala Glu Thr Gly His Leu Val
    210                 215                 220

Phe Gly Thr Leu His Thr Thr Gly Ala Ala Lys Thr Val Asp Arg Ile
225                 230                 235                 240

Val Asp Val Phe Pro Ala Gly Glu Lys Glu Met Val Arg Ser Met Leu
                245                 250                 255

Ser Glu Ser Leu Thr Ala Val Ile Ser Gln Asn Leu Leu Lys Thr His
            260                 265                 270

Asp Gly Asn Gly Arg Val Ala Ser His Glu Ile Leu Ile Ala Asn Pro
        275                 280                 285

Ala Val Arg Asn Leu Ile Arg Glu Asn Lys Ile Thr Gln Ile Asn Ser
    290                 295                 300

Val Leu Gln Thr Gly Gln Ala Ser Gly Met Gln Thr Met Asp Gln Ser
305                 310                 315                 320

Leu Gln Ser Leu Val Arg Gln Gly Leu Ile Ala Pro Glu Val Ala Arg
                325                 330                 335

Arg Arg Ala Gln Asn Ser Glu Ser Met Ser Phe
            340                 345


<210> SEQ ID NO 8
<211> LENGTH: 347
<212> TYPE: PRT
<213> ORGANISM: Ralstonia solanacearum

<400> SEQUENCE: 8

Met Asp Ile Ala Gln Leu Leu Ala Phe Ala Ala Lys Asn Lys Ala Ser
1               5                   10                  15

Asp Leu His Leu Ser Ala Gly Leu Pro Pro Met Ile Arg Ile His Gly
            20                  25                  30

Asp Met Arg Arg Ile Asn Val Pro Pro Leu Thr His Gln Asp Val His
        35                  40                  45

Ala Met Val Tyr Asp Ile Met Ser Asp Val Gln Arg Lys His Tyr Glu
    50                  55                  60

Glu Asn Leu Glu Ala Asp Phe Ser Phe Glu Ile Pro Gly Leu Ser Arg
65                  70                  75                  80

Phe Arg Val Asn Ala Phe Asn Gln Asn Arg Gly Ala Ala Ala Val Phe
                85                  90                  95

Arg Thr Ile Pro Ser Lys Val Leu Thr Leu Glu Asp Leu Lys Ala Pro
            100                 105                 110

Ala Val Phe Ser Asp Leu Ala Met Lys Pro Arg Gly Leu Val Leu Val
        115                 120                 125

Thr Gly Pro Thr Gly Ser Gly Lys Ser Thr Thr Leu Ala Ala Met Val
```

130 135 140

Asn His Arg Asn Glu Ser Asp Leu Gly His Ile Leu Thr Val Glu Asp
145 150 155 160

Pro Ile Glu Phe Val His Glu Ser Lys Lys Ser Leu Ile Asn Gln Arg
165 170 175

Glu Leu Gly Pro His Thr His Ser Phe Ala Asn Ala Leu Lys Ser Ala
180 185 190

Leu Arg Glu Asp Pro Asp Val Val Leu Val Gly Glu Leu Arg Asp Leu
195 200 205

Glu Thr Ile Arg Leu Ala Leu Thr Ala Ala Glu Thr Gly His Leu Val
210 215 220

Phe Gly Thr Leu His Thr Ser Ser Ala Ala Lys Thr Ile Asp Arg Val
225 230 235 240

Val Asp Val Phe Pro Ser Asp Glu Lys Asp Met Val Arg Thr Met Leu
245 250 255

Ser Glu Ser Leu Glu Ala Val Ile Ser Gln Thr Leu Leu Lys Thr Arg
260 265 270

Asp Gly Ser Gly Arg Val Ala Ala His Glu Ile Met Ile Cys Thr Pro
275 280 285

Ala Ile Arg His Leu Ile Arg Glu Asn Lys Ile Ser Gln Met Tyr Ser
290 295 300

Met Met Gln Thr Ser Ser Gly Leu Gly Met Gln Thr Leu Asp Gln Cys
305 310 315 320

Leu Ala Glu Leu Ile Lys Arg Ser Ala Ile Asn Tyr Ala Asp Ala Arg
325 330 335

Ala Ile Ala Lys Asn Pro Asp Ala Phe Ala Asn
340 345

<210> SEQ ID NO 9
<211> LENGTH: 345
<212> TYPE: PRT
<213> ORGANISM: Vibrio cholerae

<400> SEQUENCE: 9

Met Asp Ile Ala Glu Leu Leu Glu Phe Ser Val Lys His Asn Ala Ser
1 5 10 15

Asp Leu His Leu Ser Ala Gly Val Pro Pro Met Val Arg Ile Asp Gly
20 25 30

Glu Val Arg Lys Leu Gly Val Pro Ala Phe Thr His Ser Asp Val His
35 40 45

Arg Leu Ile Phe Glu Ile Met Asn Asp Ala Gln Arg Ser Glu Tyr Glu
50 55 60

Glu Lys Leu Glu Val Asp Phe Ser Phe Glu Leu Pro Asn Val Gly Arg
65 70 75 80

Phe Arg Val Asn Ala Phe His Gln Ala Arg Gly Cys Ser Ala Val Phe
85 90 95

Arg Thr Ile Pro Thr Val Ile Pro Thr Leu Glu Gln Leu Asp Ala Pro
100 105 110

Glu Ile Phe Ser Lys Ile Ala Asn Tyr Glu Lys Gly Leu Val Leu Val
115 120 125

Thr Gly Pro Thr Gly Ser Gly Lys Ser Thr Thr Leu Ala Ala Met Val
130 135 140

Asn Tyr Val Asn Ala His His Asn Lys His Ile Leu Thr Ile Glu Asp
145 150 155 160

```
Pro Ile Glu Phe Val His Ser Asn Asn Lys Cys Leu Ile Asn Gln Arg
                165                 170                 175

Glu Val His Arg Asp Thr His Ser Phe Lys Asn Ala Leu Arg Ser Ala
            180                 185                 190

Leu Arg Glu Asp Pro Asp Val Ile Leu Val Gly Glu Leu Arg Asp Gln
        195                 200                 205

Glu Thr Ile Ser Leu Ala Leu Thr Ala Ala Glu Thr Gly His Leu Val
    210                 215                 220

Phe Gly Thr Leu His Thr Ser Ser Ala Ala Lys Thr Ile Asp Arg Ile
225                 230                 235                 240

Ile Asp Val Phe Pro Gly Ser Asp Lys Asp Met Val Arg Ser Met Leu
                245                 250                 255

Ser Glu Ser Leu Arg Ala Val Ile Ala Gln Lys Leu Leu Lys Arg Val
            260                 265                 270

Gly Gly Gly Arg Val Ala Cys His Glu Ile Met Leu Ala Thr Pro Ala
        275                 280                 285

Ile Arg Asn Leu Ile Arg Glu Asp Lys Val Ala Gln Met Tyr Ser Ile
    290                 295                 300

Ile Gln Thr Gly Ala Ala His Gly Met Gln Thr Met Glu Gln Asn Ala
305                 310                 315                 320

Lys Gln Leu Ile Ala Arg Gly Val Val Asp Ala Gln Glu Val Gln Ser
                325                 330                 335

Lys Ile Glu Leu Asp Leu Lys Ala Phe
            340                 345


<210> SEQ ID NO 10
<211> LENGTH: 355
<212> TYPE: PRT
<213> ORGANISM: Nostoc sp.

<400> SEQUENCE: 10

Met Glu Met Met Ile Glu Asp Leu Met Glu Gln Met Ile Glu Met Gly
1               5                   10                  15

Gly Ser Asp Met His Leu Ser Ala Gly Leu Pro Pro Tyr Phe Arg Ile
            20                  25                  30

Ser Gly Lys Leu Thr Pro Ile Gly Glu Glu Val Leu Thr Ala Asp Gln
        35                  40                  45

Cys Gln Arg Leu Ile Phe Ser Met Leu Asn Asn Thr Gln Arg Lys Thr
    50                  55                  60

Leu Glu Gln Thr Trp Glu Leu Asp Cys Ser Tyr Gly Val Lys Gly Leu
65                  70                  75                  80

Ala Arg Phe Arg Val Asn Val Tyr Lys Glu Arg Gly Ala Tyr Ala Ala
                85                  90                  95

Cys Leu Arg Ala Leu Ser Ser Lys Ile Pro Asn Phe Glu Lys Leu Gly
            100                 105                 110

Leu Pro Asp Val Val Arg Glu Met Cys Asp Lys Pro Arg Gly Leu Ile
        115                 120                 125

Leu Val Thr Gly Pro Thr Gly Ser Gly Lys Thr Thr Thr Leu Ala Ala
    130                 135                 140

Met Ile Asp Leu Ile Asn Arg Thr Lys Ala Glu His Ile Leu Thr Val
145                 150                 155                 160

Glu Asp Pro Ile Glu Phe Val Tyr Glu Pro Ile Lys Ser Leu Val His
                165                 170                 175

Gln Arg Gln Leu Gly Glu Asp Thr Lys Ser Phe Ala Asn Ala Leu Lys
            180                 185                 190
```

```
Ala Ala Leu Arg Glu Asp Pro Asp Ile Val Leu Val Gly Glu Met Arg
        195                 200                 205

Asp Leu Glu Thr Ile Ser Leu Ala Ile Ser Ala Ala Glu Thr Gly His
    210                 215                 220

Leu Val Phe Gly Thr Leu His Thr Ser Ser Ala Ser Gln Thr Val Asp
225                 230                 235                 240

Arg Ile Ile Asp Val Phe Pro His Glu Lys Gln Thr Gln Val Arg Val
                245                 250                 255

Gln Leu Ser Asn Ser Leu Val Ala Val Phe Ser Gln Thr Leu Val Pro
            260                 265                 270

Lys Lys Asn Pro Lys Pro Gly Glu Tyr Gly Arg Val Met Ala Gln Glu
        275                 280                 285

Ile Met Ile Ile Thr Pro Ala Ile Ser Asn Leu Ile Arg Glu Gly Lys
    290                 295                 300

Thr Ser Gln Ile Tyr Ser Ala Ile Gln Thr Gly Gly Lys Leu Gly Met
305                 310                 315                 320

Gln Thr Leu Glu Lys Val Leu Ala Asp Tyr Tyr Lys Ser Gly Thr Ile
                325                 330                 335

Ser Phe Glu Ala Ala Met Ser Lys Thr Ser Lys Pro Asp Glu Ile Gln
            340                 345                 350

Arg Leu Ile
        355


<210> SEQ ID NO 11
<211> LENGTH: 357
<212> TYPE: PRT
<213> ORGANISM: Sulfurihydrogenibium sp.

<400> SEQUENCE: 11

Met Ala Leu Glu Tyr Met Ile Glu Asp Leu Met Glu Gln Leu Val Glu
1               5                   10                  15

Met Gly Gly Ser Asp Met His Ile Gln Ala Gly Ala Pro Val Tyr Phe
            20                  25                  30

Arg Val Ser Gly Lys Leu Glu Pro Ile Asn Glu Glu Val Leu Thr Pro
        35                  40                  45

Gln Glu Ser Gln Lys Leu Ile Phe Ser Met Leu Asn Asn Ser Gln Arg
    50                  55                  60

Lys Glu Leu Glu Gln Asn Trp Glu Leu Asp Cys Ser Tyr Gly Val Lys
65                  70                  75                  80

Gly Leu Ala Arg Phe Arg Ile Asn Val Tyr Lys Glu Arg Gly Cys Tyr
                85                  90                  95

Ala Ala Cys Leu Arg Ala Leu Ser Ser Lys Ile Pro Asn Phe Glu Gln
            100                 105                 110

Leu Gly Leu Pro Asn Ile Val Arg Glu Met Ala Glu Arg Pro Arg Gly
        115                 120                 125

Leu Ile Leu Val Thr Gly Gln Thr Gly Ser Gly Lys Thr Thr Thr Leu
    130                 135                 140

Ala Ala Ile Leu Asp Leu Ile Asn Arg Thr Arg Ala Glu His Ile Leu
145                 150                 155                 160

Thr Ile Glu Asp Pro Ile Glu Tyr Val Phe Pro Asn Val Arg Ser Leu
                165                 170                 175

Phe His Gln Arg Gln Arg Gly Glu Asp Thr Lys Ser Phe Ser Asn Ala
            180                 185                 190

Leu Arg Ala Ala Leu Arg Glu Asp Pro Asp Ile Val Leu Val Gly Glu
```

```
        195                 200                 205

Leu Arg Asp Leu Glu Thr Ile Ala Leu Ala Ile Thr Ala Ala Glu Thr
    210                 215                 220

Gly His Leu Val Phe Gly Thr Leu His Thr Asn Ser Ala Ala Gly Thr
225                 230                 235                 240

Ile Asp Arg Met Leu Asp Val Phe Pro Ala Asn Gln Gln Ala Gln Ile
                245                 250                 255

Arg Ala Met Leu Ser Asn Ser Leu Leu Ala Val Phe Ala Gln Asn Leu
            260                 265                 270

Val Lys Lys Lys Ser Pro Lys Pro Gly Glu Phe Gly Arg Ala Leu Val
        275                 280                 285

Gln Glu Ile Met Val Ile Thr Pro Ala Ile Ala Asn Leu Ile Arg Glu
    290                 295                 300

Gly Lys Ala Ala Gln Ile Tyr Ser Ala Ile Gln Thr Gly Ala Lys Leu
305                 310                 315                 320

Gly Met Gln Thr Met Glu Gln Gly Leu Ala Thr Leu Val Val Ser Gly
                325                 330                 335

Val Ile Ser Leu Glu Glu Gly Leu Ala Lys Ser Gly Lys Pro Asp Glu
            340                 345                 350

Leu Gln Arg Leu Ile
        355


<210> SEQ ID NO 12
<211> LENGTH: 351
<212> TYPE: PRT
<213> ORGANISM: Aquifex aeolicus
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (307)..(307)
<223> OTHER INFORMATION: Xaa can be any naturally occurring amino acid
<220> FEATURE:
<221> NAME/KEY: misc_feature
<222> LOCATION: (316)..(316)
<223> OTHER INFORMATION: Xaa can be any naturally occurring amino acid
<220> FEATURE:
<221> NAME/KEY: misc_feature
<222> LOCATION: (319)..(319)
<223> OTHER INFORMATION: Xaa can be any naturally occurring amino acid
<220> FEATURE:
<221> NAME/KEY: misc_feature
<222> LOCATION: (338)..(338)
<223> OTHER INFORMATION: Xaa can be any naturally occurring amino acid
<220> FEATURE:
<221> NAME/KEY: misc_feature
<222> LOCATION: (350)..(350)
<223> OTHER INFORMATION: Xaa can be any naturally occurring amino acid

<400> SEQUENCE: 12

Glu Leu Lys Ile Leu Glu Ile Ile Lys Glu Ala Ile Glu Leu Gly Ala
1               5                   10                  15
```

-continued

```
Ser Asp Ile His Leu Thr Ala Gly Ala Pro Pro Ala Val Arg Ile Asp
            20                  25                  30

Gly Tyr Ile Lys Phe Leu Lys Asp Phe Pro Arg Leu Thr Pro Glu Asp
        35                  40                  45

Thr Gln Lys Leu Ala Tyr Ser Val Xaa Ser Glu Lys His Arg Gln Lys
    50                  55                  60

Leu Glu Glu Asn Gly Gln Val Asp Phe Ser Phe Gly Val Arg Gly Val
65                  70                  75                  80

Gly Arg Phe Arg Ala Asn Val Phe Tyr Gln Arg Gly Ser Val Ala Ala
                85                  90                  95

Ala Leu Arg Ser Leu Pro Ala Glu Ile Pro Glu Phe Lys Lys Leu Gly
            100                 105                 110

Leu Pro Asp Lys Val Leu Glu Leu Cys His Arg Lys Xaa Gly Leu Ile
        115                 120                 125

Leu Val Thr Gly Pro Thr Gly Ser Gly Lys Ser Thr Thr Ile Ala Ser
    130                 135                 140

Xaa Ile Asp Tyr Ile Asn Gln Thr Lys Ser Tyr His Ile Ile Thr Ile
145                 150                 155                 160

Glu Asp Pro Ile Glu Tyr Val Phe Lys His Lys Lys Ser Ile Val Asn
                165                 170                 175

Gln Arg Glu Val Gly Glu Asp Thr Lys Ser Phe Ala Asp Ala Leu Arg
            180                 185                 190

Ala Ala Leu Arg Glu Asp Pro Asp Val Ile Phe Val Gly Glu Xaa Arg
        195                 200                 205

Asp Leu Glu Thr Val Glu Thr Ala Leu Arg Ala Ala Glu Thr Gly His
    210                 215                 220

Leu Val Phe Gly Thr Leu His Thr Asn Thr Ala Ile Asp Thr Ile His
225                 230                 235                 240

Arg Ile Val Asp Ile Phe Pro Leu Asn Gln Gln Glu Gln Val Arg Ile
                245                 250                 255

Val Leu Ser Phe Ile Leu Gln Gly Ile Ile Ser Gln Arg Leu Leu Pro
            260                 265                 270

Lys Ile Gly Gly Gly Arg Val Leu Ala Tyr Glu Leu Leu Ile Pro Asn
        275                 280                 285

Thr Ala Ile Arg Asn Leu Ile Arg Glu Asn Lys Leu Gln Gln Val Tyr
    290                 295                 300

Ser Leu Xaa Gln Ser Gly Gln Ala Glu Thr Gly Xaa Gln Thr Xaa Asn
305                 310                 315                 320

Gln Thr Leu Tyr Lys Leu Tyr Lys Gln Gly Leu Ile Thr Leu Glu Asp
                325                 330                 335

Ala Xaa Glu Ala Ser Pro Asp Pro Lys Glu Leu Glu Arg Xaa Ile
            340                 345                 350
```